(12) United States Patent
McKernan et al.

(10) Patent No.: US 7,056,340 B2
(45) Date of Patent: *Jun. 6, 2006

(54) METHOD FOR FIXING A GRAFT IN A BONE TUNNEL

(75) Inventors: Daniel J. McKernan, Sylvania, OH (US); Gregory R. Whittaker, Stoneham, MA (US); Harold M. Martins, Newton, MA (US); Joan M. Sullivan, Hanover, MA (US); Ronald L. Taylor, Jr., Everett, MA (US)

(73) Assignee: Ethicon, Inc., Somerville, NJ (US)

( * ) Notice: Subject to any disclaimer, the term of this patent is extended or adjusted under 35 U.S.C. 154(b) by 0 days.

This patent is subject to a terminal disclaimer.

(21) Appl. No.: 10/137,505

(22) Filed: Apr. 30, 2002

(65) Prior Publication Data

US 2003/0009217 A1 Jan. 9, 2003

Related U.S. Application Data

(60) Continuation of application No. 09/577,757, filed on May 23, 2000, now Pat. No. 6,379,384, which is a division of application No. 09/015,493, filed on Jan. 28, 1998, now Pat. No. 6,066,173.

(51) Int. Cl.
*A61F 2/08* (2006.01)

(52) U.S. Cl. .................................. 623/13.12; 623/13.14
(58) Field of Classification Search .............. 623/13.11, 623/13.12, 13.1, 13.19; 606/80, 90, 98, 102
See application file for complete search history.

(56) References Cited

U.S. PATENT DOCUMENTS 3,973,277 A 8/1976 Semple et al.
4,257,411 A 3/1981 Cho
4,858,603 A 8/1989 Clemow et al.
4,898,156 A 2/1990 Gatturna et al.
4,899,743 A 2/1990 Nicholson et al.
4,901,711 A 2/1990 Goble et al.
4,944,742 A 7/1990 Clemow et al.
4,950,270 A 8/1990 Bowman et al.
4,968,315 A 11/1990 Gatturna
4,985,032 A 1/1991 Goble
5,004,474 A 4/1991 Fronk et al.
5,067,962 A 11/1991 Campbell et al.
5,147,362 A 9/1992 Goble
5,152,764 A 10/1992 Goble
5,234,434 A 8/1993 Goble et al.
5,266,075 A 11/1993 Clark et al.

(Continued)

FOREIGN PATENT DOCUMENTS

| EP | 0463551 | 1/1992 |
|---|---|---|
| EP | 0469551 B1 | 12/1994 |
| EP | 0469511 B1 | 12/1996 |
| FR | 2598311 | 11/1987 |
| WO | WO 9830162 | 7/1998 |

OTHER PUBLICATIONS

Stedmans Medical Dictionary 26th Edition p. 1816.*

*Primary Examiner*—Suzette J. Jackson
(74) *Attorney, Agent, or Firm*—Pandiscio & Pandiscio

(57) ABSTRACT

A method for fixing a portion of a piece of tissue in a bone tunnel comprising the steps of placing the portion of a piece of tissue in the bone tunnel, advancing spaced-apart first and second metal wires though the bone, transversely of the bone tunnel, so as to intersect the bone tunnel and extend into the portion of a piece of tissue, removing one of the wires and replacing the one removed wire with a first rod, and removing the other of the wires and replacing the other removed wire with a second rod, whereby to retain the portion of a piece of tissue in the bone tunnel with the rods.

5 Claims, 48 Drawing Sheets

U.S. PATENT DOCUMENTS

| | | | |
|---|---|---|---|
| 5,300,077 A | | 4/1994 | Howell |
| 5,350,380 A | | 9/1994 | Goble et al. |
| 5,354,300 A | | 10/1994 | Goble et al. |
| 5,356,413 A | | 10/1994 | Martins et al. |
| 5,356,435 A | | 10/1994 | Thein |
| 5,364,400 A | | 11/1994 | Rego, Jr. et al. |
| 5,372,599 A | | 12/1994 | Martins |
| 5,376,119 A | * | 12/1994 | Zimmermann et al. ....... 606/73 |
| 5,393,302 A | | 2/1995 | Clark et al. |
| 5,397,356 A | * | 3/1995 | Goble et al. ................... 606/73 |
| 5,431,651 A | | 7/1995 | Goble |
| 5,470,334 A | | 11/1995 | Ross et al. |
| 5,522,817 A | | 6/1996 | Sander et al. |
| 5,643,266 A | * | 7/1997 | Li ............................... 606/72 |
| 5,672,158 A | | 9/1997 | Okada et al. |
| 5,674,224 A | | 10/1997 | Howell et al. |
| 5,688,284 A | | 11/1997 | Chervitz et al. |
| 5,697,933 A | | 12/1997 | Gundlapalli et al. |
| 5,849,013 A | | 12/1998 | Whittaker |
| 5,891,150 A | | 4/1999 | Chan |
| 5,918,604 A | * | 7/1999 | Whelan ....................... 128/898 |
| 6,019,767 A | | 2/2000 | Howell |
| 6,066,173 A | * | 5/2000 | McKernan et al. ...... 623/13.14 |
| 6,113,604 A | | 9/2000 | Whittaker et al. |
| 6,132,433 A | * | 10/2000 | Whelan ....................... 606/72 |
| 6,306,138 B1 | | 10/2001 | Clark et al. |
| 6,379,384 B1 | * | 4/2002 | McKernan et al. ...... 623/13.12 |
| 6,517,546 B1 | | 2/2003 | Whittaker et al. |
| 6,537,319 B1 | * | 3/2003 | Whelan ................... 623/13.12 |

* cited by examiner

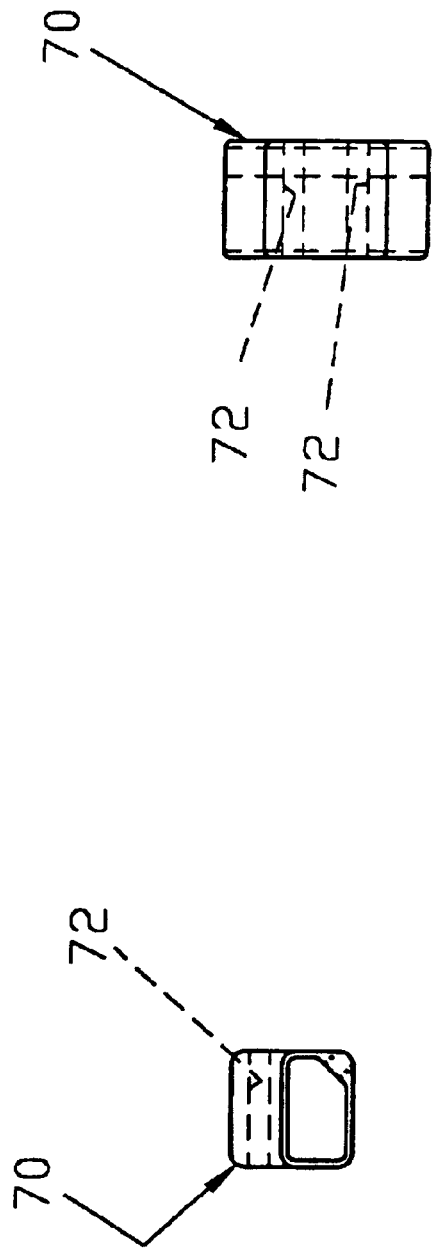
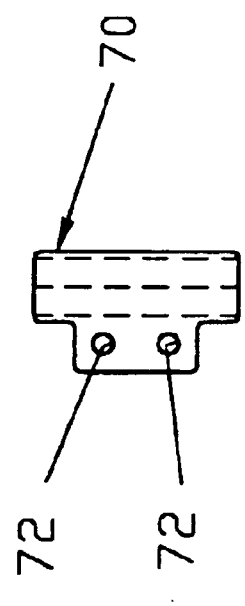
FIG. 13
FIG. 14
FIG. 12

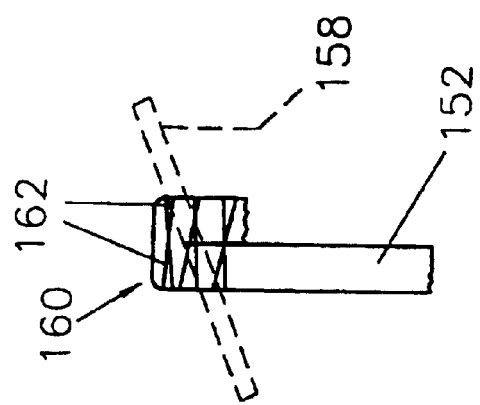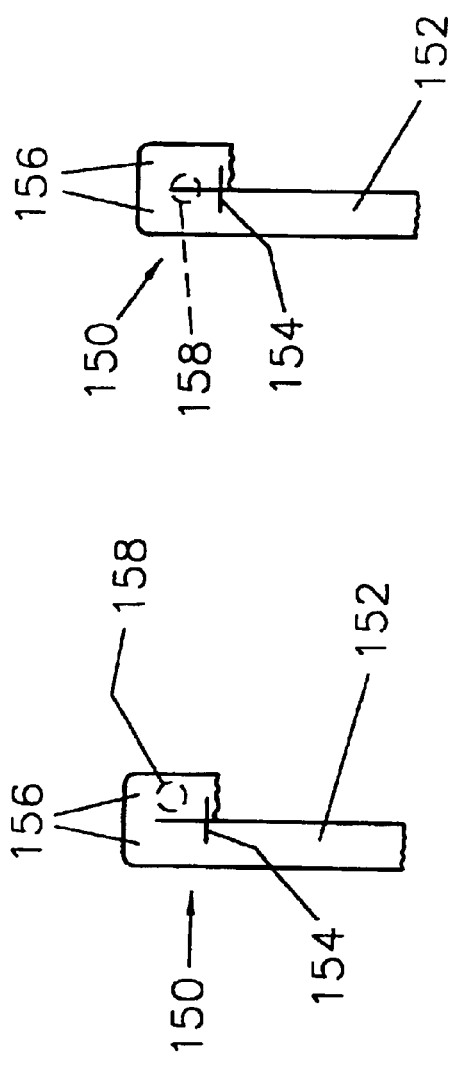

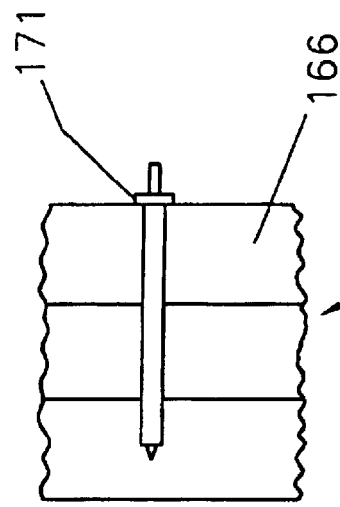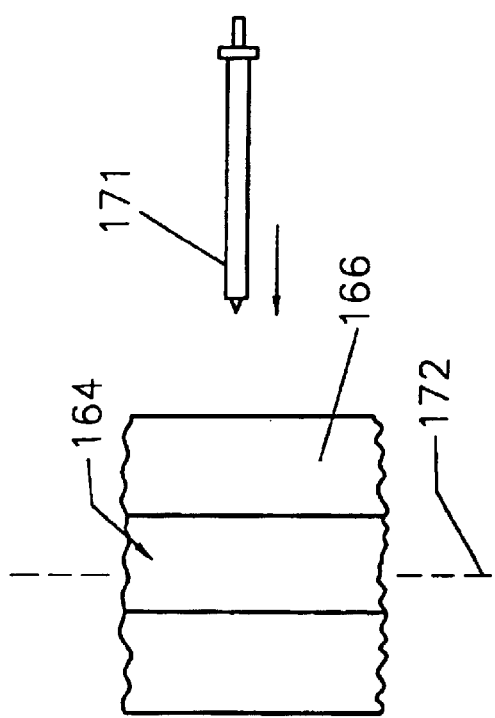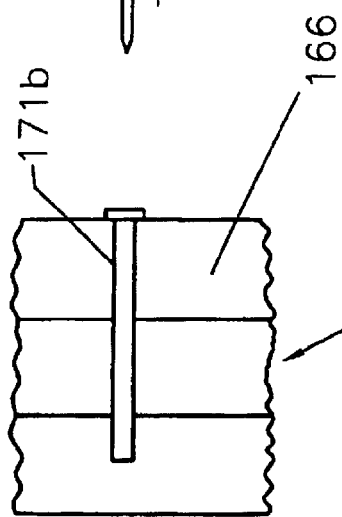
FIG. 44
FIG. 45
FIG. 46

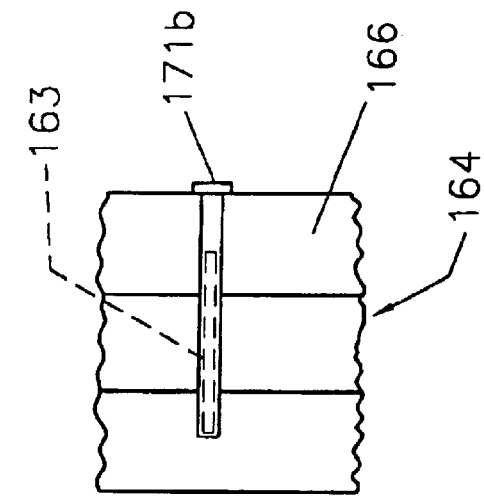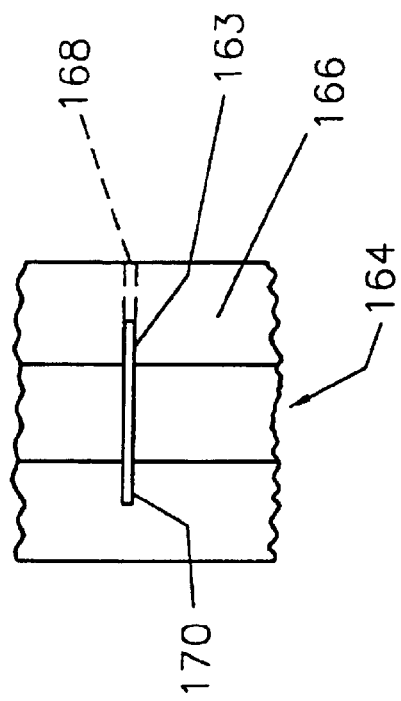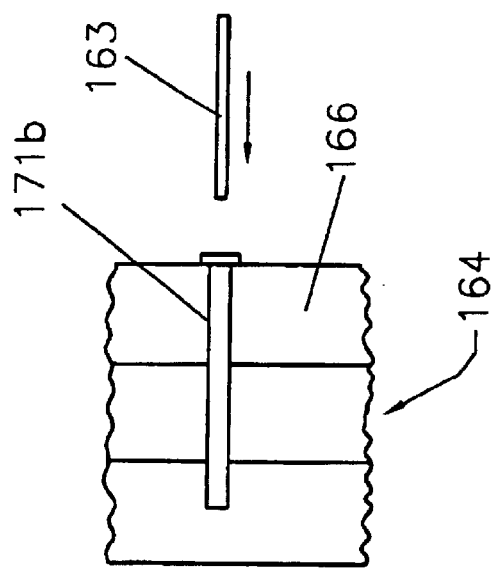

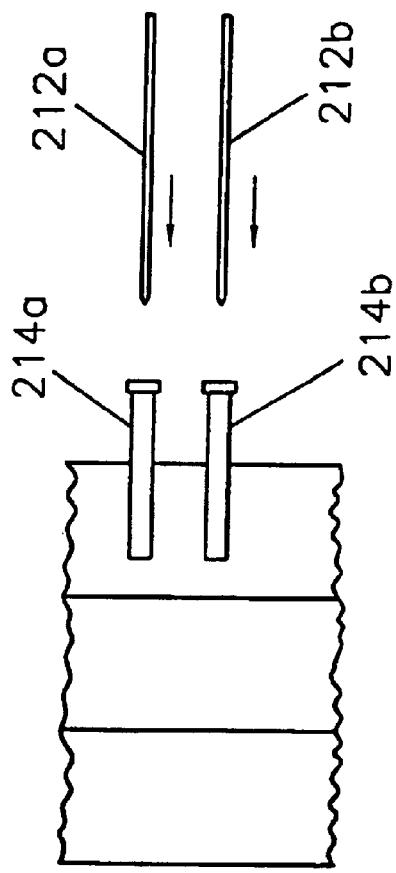
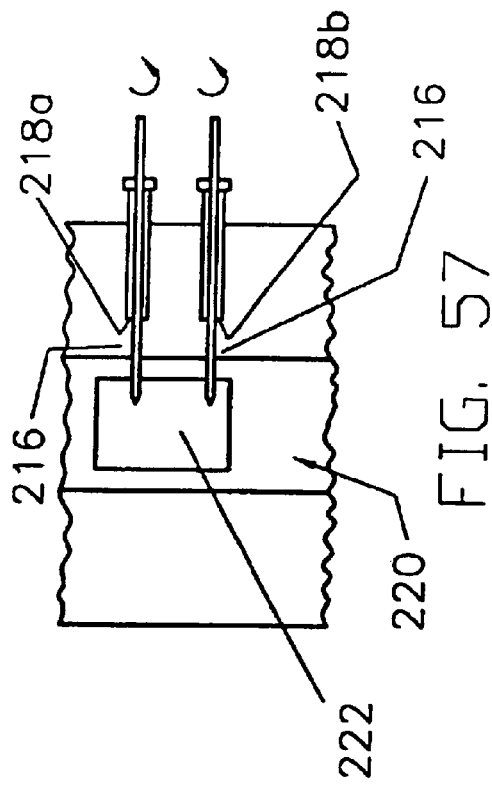
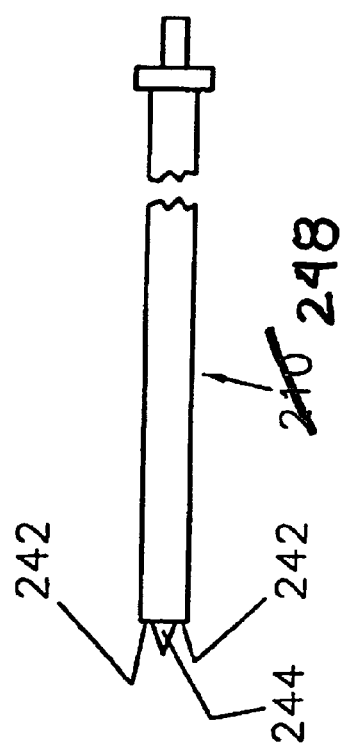
FIG. 56
FIG. 57
FIG. 55

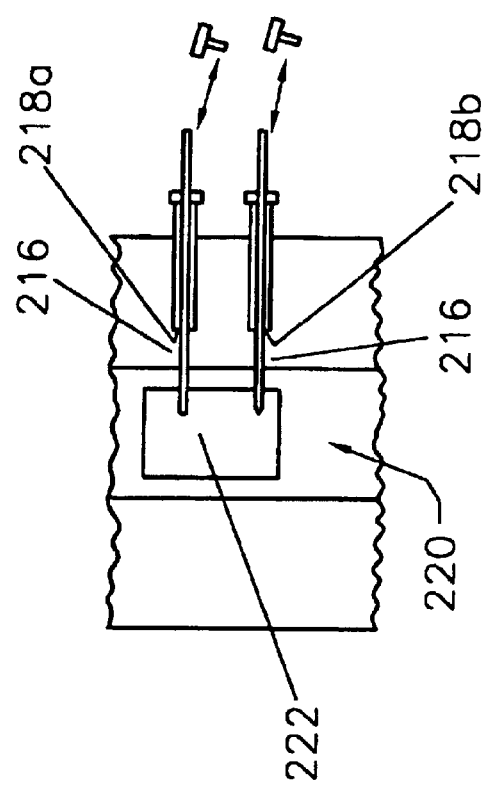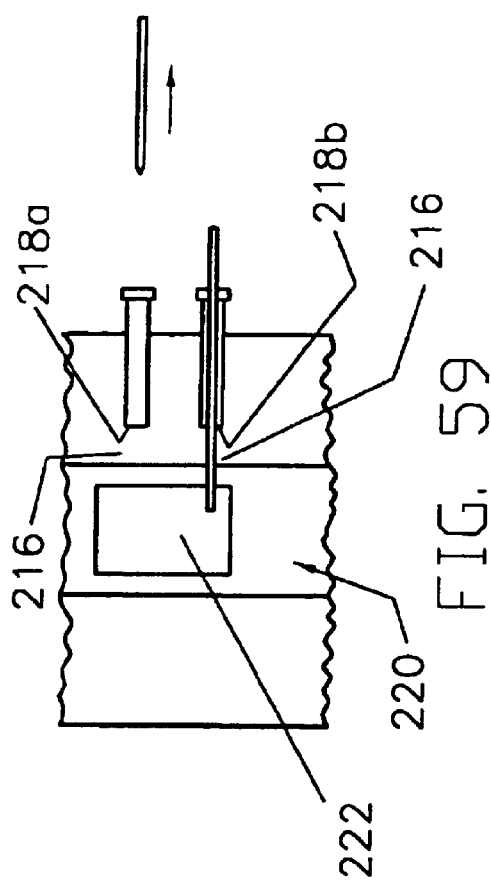

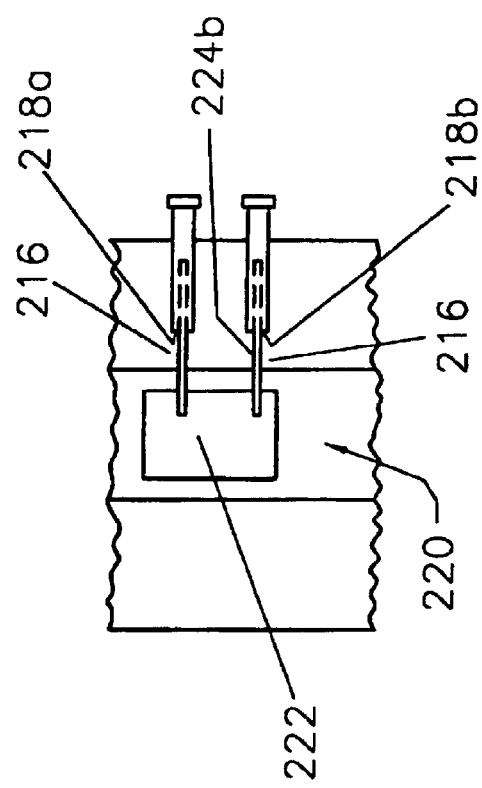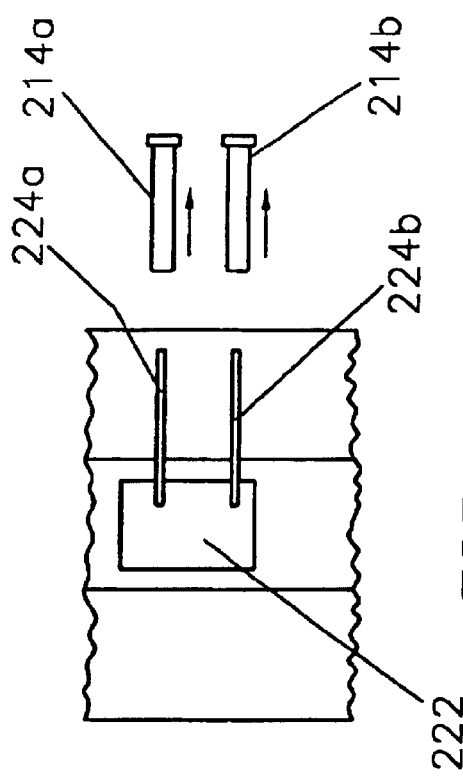

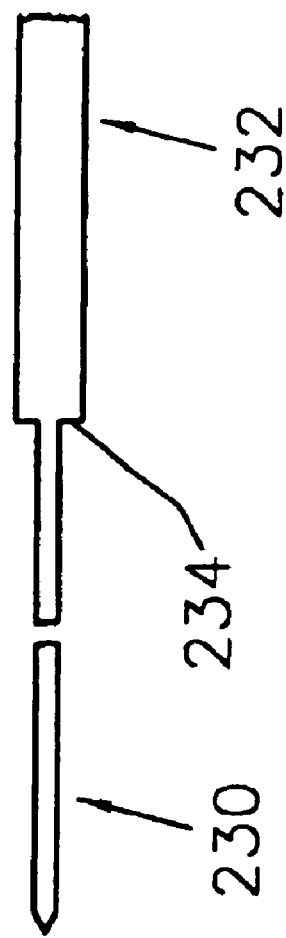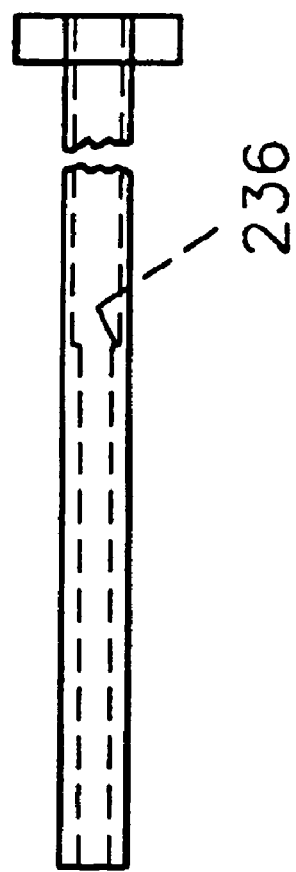

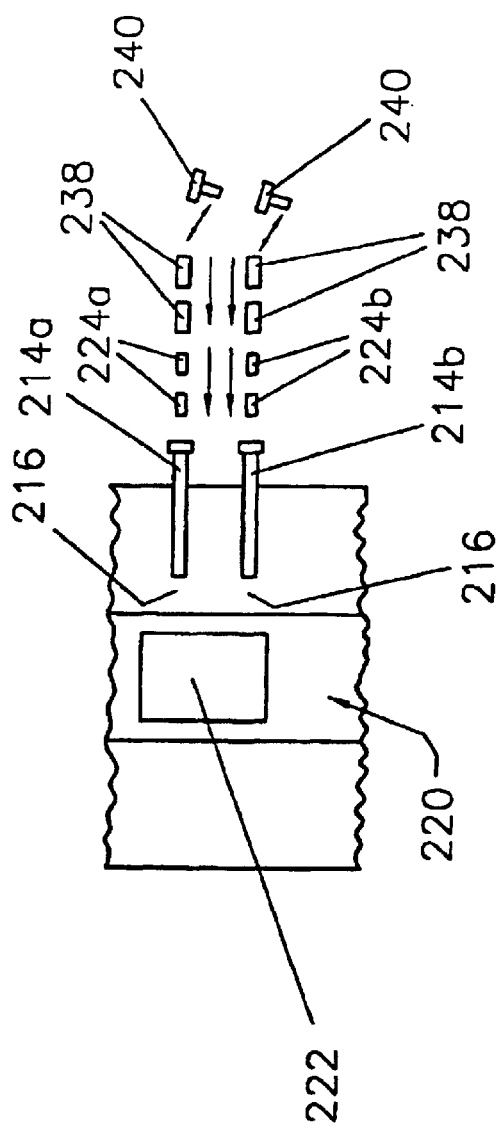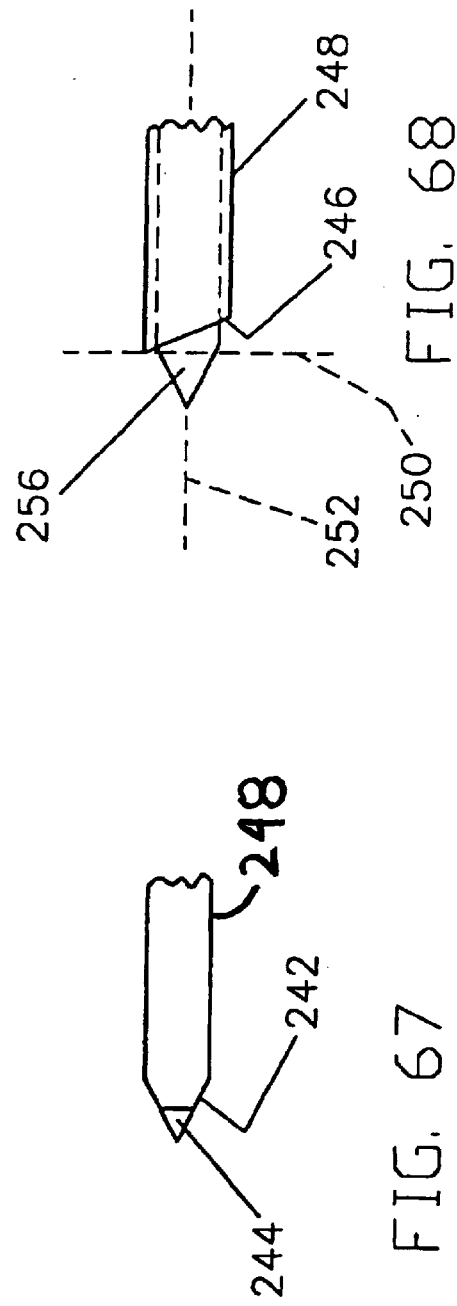

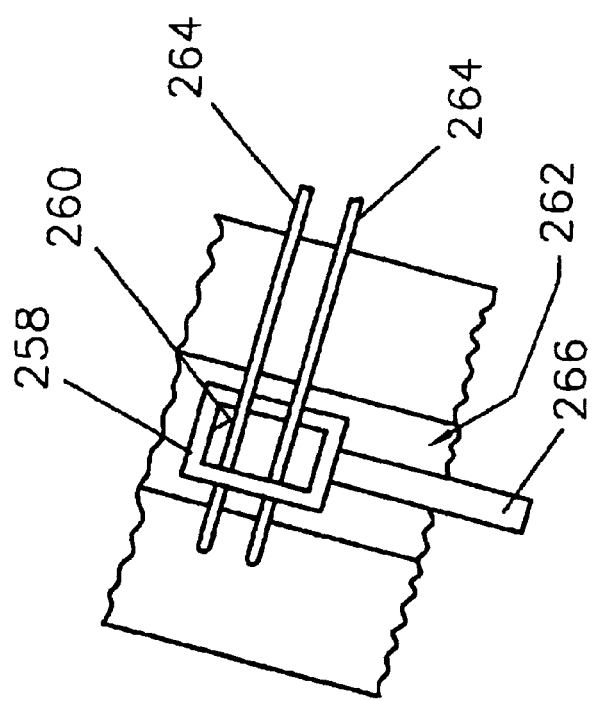
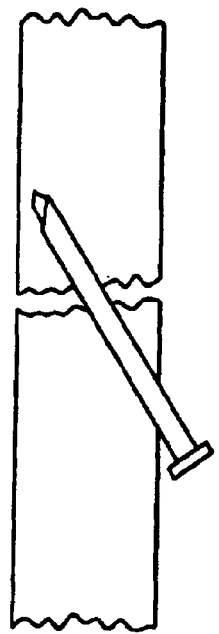
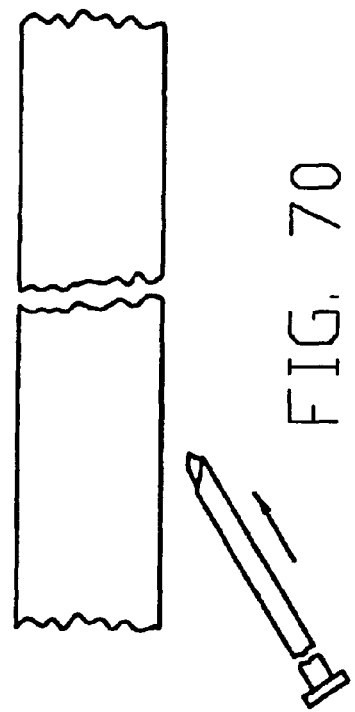
FIG. 69
FIG. 70
FIG. 71

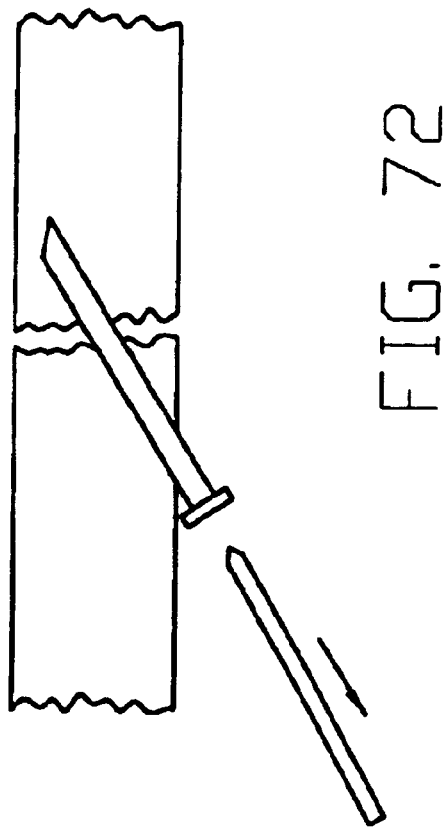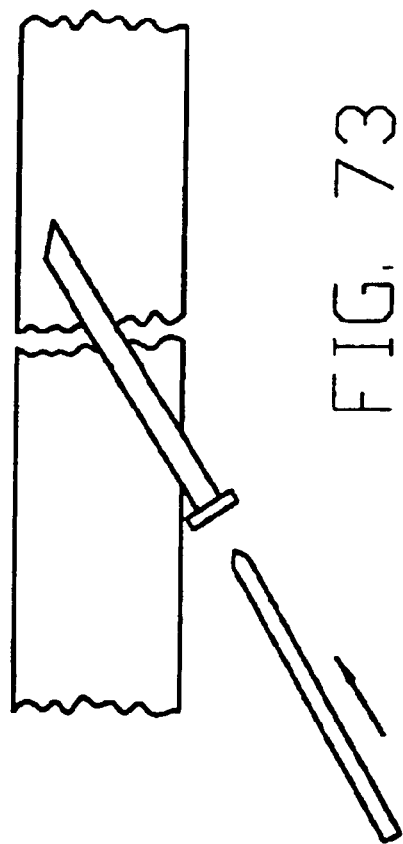

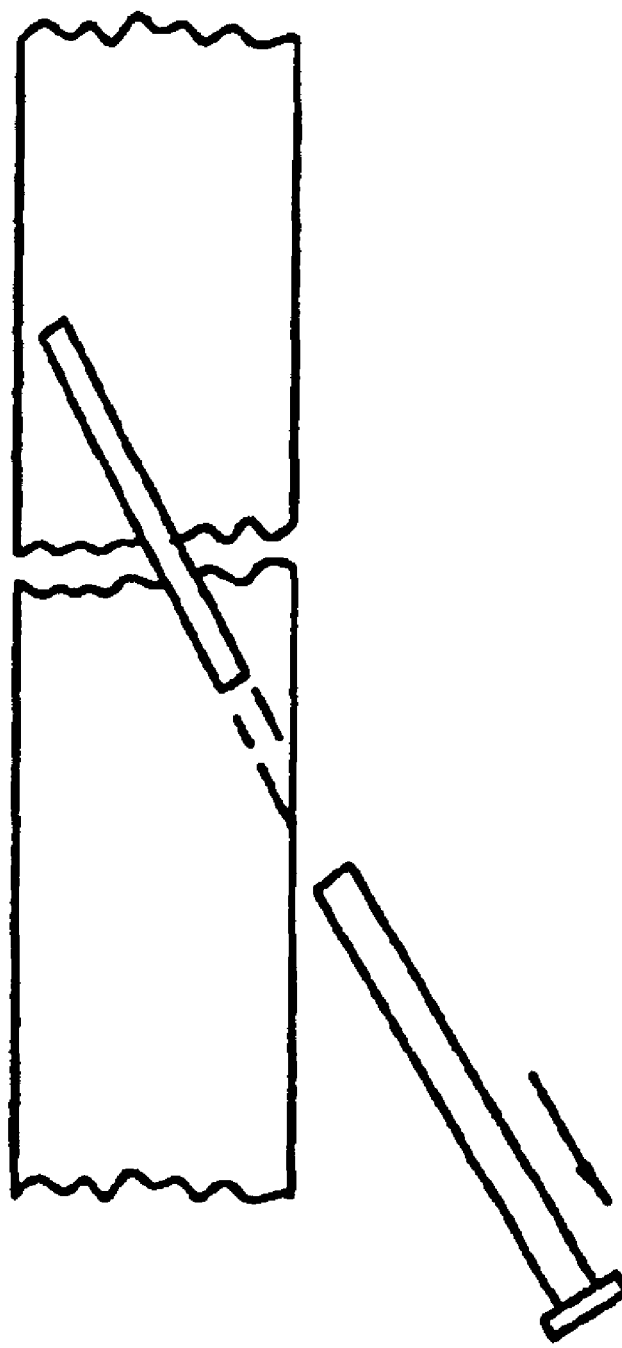

METHOD FOR FIXING A GRAFT IN A BONE TUNNEL

This is a continuation of U.S. patent application Ser. No. 09/577,757, filed May 23, 2000 now U.S. Pat. No. 6,379,384 by Daniel J. McKernan et al. for METHOD AND APPARATUS FOR FIXING A GRAFT IN A BONE TUNNEL, which is in turn a division of prior application Ser. No. 09/015,493, filed Jan. 28, 1998 now U.S. Pat. No. 6,066,173 by Daniel J. McKernan et al. for METHOD AND APPARATUS FOR FIXING A GRAFT IN A BONE TUNNEL.

FIELD OF THE INVENTION

This invention relates to surgical methods in general, and more particularly to methods and apparatus for fixing bone blocks in bone tunnels.

BACKGROUND OF THE INVENTION

The complete or partial detachment of ligaments, tendons and/or other soft tissues from their associated bones within the body are relatively commonplace injuries. Tissue detachment may occur as the result of an accident such as a fall, overexertion during a work-related activity, during the course of an athletic event, or in any one of many other situations and/or activities. Such injuries are generally the result of excess stress being placed on the tissues.

In the case of a partial detachment, commonly referred to under the general term "sprain", the injury frequently heals itself, if given sufficient time, and if care is taken not to expose the injury to undue stress during the healing process. If, however, the ligament or tendon is completely detached from its associated bone or bones, or if it is severed as the result of a traumatic injury, partial or permanent disability may result. Fortunately, a number of surgical procedures exist for re-attaching such detached tissues and/or completely replacing severely damaged tissues.

One such procedure involves the re-attachment of the detached tissue using "traditional" attachment devices such as staples, sutures and/or cancellous bone screws. Such traditional attachment devices have also been used to attach tendon or ligament grafts (often formed from autogenous tissue harvested from elsewhere in the body) to the desired bone or bones.

Another procedure is described in U.S. Pat. No. 4,950,270, issued Aug. 21, 1990 to Jerald A. Bowman et al. In this procedure, the damaged anterior cruciate ligament ("ACL") in a human knee, for example, is replaced by first forming bone tunnels through the tibia and femur at the points of normal attachment of the anterior cruciate ligament. Next, a ligament graft with a bone block on one of its ends is sized so as to fit within the bone tunnels. Suture is then attached to the bone block and thereafter passed through the tibial and femoral bone tunnels. The bone block is then drawn through the tibial tunnel and up into the femoral tunnel using the suture. As this is done, the graft ligament extends back out of the femoral tunnel, across the interior of the knee joint, and then through the tibial tunnel. The free end of the graft ligament resides outside the tibia, at the anterior side of the tibia. Next, a bone screw is inserted between the bone block and the wall of femoral bone tunnel so as to securely lock the bone block in position by a tight interference fit. Finally, the free end of the graft ligament is securely attached to the tibia.

In U.S. Pat. No. 5,147,362, issued Sep. 15, 1992 to E. Marlowe Goble, there is disclosed a procedure wherein aligned femoral and tibial tunnels are formed in a human knee. A bone block with a graft ligament attached thereto is passed through the tunnels to a blind end of the femoral tunnel where the block is fixed in place by an anchor. The ligament extends out the tibial tunnel, and the end thereof is attached to the tibial cortex by staples or the like. Alternatively, the end of the ligament may be fixed in the tibial tunnel by an anchor or by an interference screw.

Various types of ligament and/or suture anchors, and anchors for attaching other objects to bone, are also well known in the art. A number of these devices are described in detail in U.S. Pat. Nos. 4,898,156; 4,899,743; 4,968,315; 5,356,413; and 5,372,599, each of which is presently owned by Mitek Surgical Products, Inc. of Westwood, Mass., the assignee of this patent application.

One known method for anchoring bone blocks in bone tunnels is through "cross-pinning", in which a pin, screw or rod is driven into the bone transversely to the bone tunnel so as to intersect the bone block and thereby cross-pin the bone block in the bone tunnel. In order to provide for proper cross-pinning of the bone block in the bone tunnel, a drill guide is generally used. The drill guide serves to ensure that the transverse passage is positioned in the bone so that it will intersect the appropriate tunnel section and the bone block. Drill guides for use in effecting such transverse drilling are shown in U.S. Pat. Nos. 4,901,711; 4,985,032; 5,152,764; 5,350,380; and 5,431,651.

Other patents in which cross-pinning is discussed include U.S. Pat. Nos. 3,973,277; 5,004,474; 5,067,962; 5,266,075; 5,356,435; 5,376,119; 5,393,302; and 5,397,356.

In U.S. Pat. No. 5,431,651, issued Jul. 11, 1995 to E. Marlowe Goble, it is said that a cross-pin screw may be formed out of a material which may be absorbed by the body over time, thereby eliminating any need for the cross-pin screw to be removed in a subsequent surgical procedure.

However, such absorbable cross-pin screws as are presently known in the art lack sufficient strength to be passed directly into the bone and the bone block. Accordingly, to use absorbable cross-pin screws, one must first drill a hard metal drilling implement into the bone and bone block, remove the drilling implement, and then replace the drilling implement with the absorbable cross-pin screw. However, removal of the hard metal drilling implement often permits the bone block to shift in the tunnel, such that the subsequent insertion of the absorbable cross-pin screw becomes impossible.

Accordingly, there exists a need for a method and apparatus for fixing a bone block in a bone tunnel such that upon completion of the procedure, the bone block is cross-pinned in the bone tunnel by elements which are made of absorbable material.

OBJECTS OF THE INVENTION

The object of the present invention is, therefore, to provide a method for fixing a bone block in a bone tunnel such that the bone block is retained in the tunnel by cross-pins which are made of a material which is absorbable by the body.

SUMMARY OF THE INVENTION

These and other objects of: the present invention are addressed by the provision and use of a novel method for fixing a bone block in a bone tunnel.

In one form of the invention, the novel method comprises the steps of placing the bone block in the bone tunnel, and then advancing spaced-apart first and second drill means through the bone transversely of the bone tunnel so as to intersect the bone block and extend therethrough. The method further includes the steps of removing one of the drill means and replacing the one removed drill means with a first absorbable rod, and then removing the other of the drill means and replacing the other removed drill means with a second absorbable rod, whereby the bone block will be retained in the bone tunnel with the absorbable rods. In one form of the invention, the first and second drill means may comprise metal wires.

The objects of the present invention are further addressed by the provision and use of an alternative method for fixing a bone block in a bone tunnel. The method comprises the steps of placing the bone block in the bone tunnel, and then advancing spaced-apart first and second trocar and sleeve assemblies through the bone, transversely of the bone tunnel, so as to intersect the bone block and extend therethrough, the trocar in each of the assemblies being disposed within one of the sleeves of the assemblies and substantially filling the sleeve. The method further includes the steps of removing the trocar from the first of the sleeves, advancing a first absorbable rod through the first sleeve and through the bone block, and then removing the first sleeve, so as to leave the first absorbable rod in the bone and the bone block. The method further includes the steps of removing the trocar from the second of the sleeves, advancing a second absorbable rod through the second sleeve and through the bone block, and then removing the second sleeve, so as to leave the second absorbable rod in the bone and the bone block, whereby the bone block will be retained in the bone tunnel with the absorbable rods.

The objects of the present invention are further addressed by the provision and use of another alternative method for fixing a bone block in a bone tunnel. The method comprises the steps of placing the bone block in the bone tunnel, and then advancing spaced-apart first and second trocar and sleeve assemblies through the bone transversely of the bone tunnel so as to intersect the bone block and extend therethrough, the trocar in each of the assemblies being disposed within one of the sleeves of the assemblies and substantially filling the sleeve. The method further includes the steps of removing the trocar from the sleeves, advancing absorbable rods through the sleeves and through the bone block, and then removing the sleeves from the bone block and the bone, so as to leave the absorbable rods in the bone block and the bone, whereby the bone block will be retained in the bone tunnel with the absorbable rods.

In accordance with a still further feature of the present invention, there is provided another rack assembly for cross-pinning a bone block in a bone tunnel in a human femur. The rack assembly comprises an L-shaped member having a base portion and an arm portion extending transversely of the base portion, and a cannulated sleeve for movement through the femur until a free end thereof is disposed adjacent to the bone block, with an opposite end thereof being connectable to the base portion of the L-shaped member. A trocar sleeve guide member is removably connectable to the arm portion of the L-shaped member and is provided with bores extending therethrough at an angle normal to a hypothetical extension of a longitudinal axis of the cannulated sleeve. First and second trocar sleeves are provided for movable disposition in the bores, respectively. At least one trocar is provided for disposition in the trocar sleeves, the trocar being interconnectable with the trocar sleeve in which the trocar is disposed such that the trocar sleeve and the trocar therein are movable axially toward the bone block and rotatable together, such that the interconnected trocar and trocar sleeve are adapted for drilling into the femur and the bone block. The trocar is removable from the trocar sleeves, and absorbable rods are slidable through the trocar sleeves and through the bone block, the trocar sleeves being removable from the bone block and the femur and from the absorbable rods so as to leave the absorbable rods in the bone block and the femur.

In accordance with a further feature of the invention, there is provided a method for fixing a portion of a piece of tissue in a bone tunnel in a bone, the method comprising the steps of:

placing the portion of a piece of tissue in the bone tunnel;

advancing spaced-apart, first and second drill means through the bone transversely of the bone tunnel so as to intersect and extend into the tissue;

removing one of the drill means and replacing the one removed drill means with a first rod; and removing the other of the drill means and replacing the other removed drill means with a second rod;

whereby to retain the portion of a piece of tissue in the bone tunnel with the rods.

In accordance with a further feature of the invention, there is provided a method for fixing a portion of a piece of tissue in a bone tunnel in a bone, the method comprising the steps of:

placing the portion of a piece of tissue in the bone tunnel;

advancing a first drill means through a first portion of the bone and transversely of the tunnel so as to intersect and extend into the portion of a piece of tissue;

advancing a second drill means through a second portion of the bone and transversely of the tunnel so as to intersect and extend into the portion of a piece of tissue, the second drill means being spaced from the first drill means;

removing one of the first and second drill means while leaving the other of the first and second drill means in place in the bone and the portion of a piece of tissue;

advancing a first rod through a bore left by removal of the one drill means, such that the first rod extends through the bone and into the portion of a piece of tissue;

removing the other of the first and second drill means; and advancing a second rod through a bore left by removal of the other drill means, such that the second rod extends through the bone and into the portion of a piece of tissue;

whereby to retain the portion of a piece of tissue in the bone tunnel with the rods.

In accordance with a further feature of the invention, there is provided a method for fixing a portion of a piece of tissue in a bone tunnel in a bone, the method comprising the steps of:

(a) placing the portion of a piece of tissue in the bone tunnel;

(b) advancing a plurality of drill means through the bone transversely of the tunnel so as to intercept and extend into the portion of a piece of tissue;

(c) removing at least one of the drill means while leaving at least one of the drill means in place, and replacing the removed at least one drill means with at least one rod;

(d) removing at least one further of the drill means and replacing the at least one further of the drill means with at least one further rod; and (e) repeating step (d), if and as desired, until a selected number of the drill means each is replaced by a rod, whereby to retain the portion a piece of tissue in the bone tunnel with the rods.

In accordance with a further feature of the invention, there is provided a method for fixing a portion of a piece of tissue tunnel in a bone, the method comprising the steps of:

placing a portion of a piece of tissue in the bone tunnel;

advancing spaced-apart, first and second trocar and sleeve assemblies through the bone transversely of the bone tunnel so as to intersect and extend into the portion of a piece of tissue, the trocar in each of the assemblies being disposed within one of the sleeves of the assemblies and substantially filling the sleeve;

removing the trocar from the first of the sleeves, advancing a first rod through the first sleeve and into the portion of a piece of tissue, and then removing the first sleeve, so as to leave the first rod in the bone and the portion of a piece of tissue; and removing the trocar from the second of the sleeves, advancing a second rod through the second sleeve and into the portion of a piece of tissue, and then removing the second sleeve, so as to leave the second rod in the bone and the portion of a piece of tissue, whereby to retain the portion of a piece of tissue in the tunnel with the rods.

In accordance with a further feature of the invention, there is provided a method for fixing a portion of a piece of tissue in a bone tunnel in a bone, the method comprising the steps of:

placing a portion of a piece of tissue in the bone tunnel;

advancing spaced-apart, first and second trocar and sleeve assemblies thorough the bone transversely of the bone tunnel so as to intersect and extend into the portion of a piece of tissue, the trocar in each of the assemblies being disposed within one of the sleeves of the assemblies and substantially filling the sleeve;

removing the trocar from the sleeves;

advancing rods through the sleeves and into the portion of a piece of tissue; and removing the sleeves from the portion of a piece of tissue and the bone and the rods so as to leave the rods in the portion of a piece of tissue and the bone, whereby to retain the portion of a piece of tissue in the tunnel with the rods.

In accordance with a further feature of the invention, there is provided a method for fixing a portion of a piece of tissue in a bone tunnel in a bone covered by skin, the method comprising the steps of:

placing the portion of a piece of tissue in the bone tunnel;

advancing a trocar and sleeve assembly through the skin and through the bone transversely of the bone tunnel so as to intersect the portion of a piece of tissue and extend at least partially therethrough, the trocar of the assembly being disposed within the sleeve of the assembly;

removing the trocar from the sleeve;

advancing a rod through the sleeve and through the skin and into the portion of a piece of tissue; and removing the sleeve, so as to leave the rod in the bone and the portion of the piece of tissue, whereby to retain the portion of the piece of tissue in the bone tunnel.

In accordance with a further feature of the invention, there is provided a method for fixing a portion of a piece of tissue in a bone tunnel in a bone, the method comprising the steps of:

placing the portion of a piece of tissue in the bone tunnel;

advancing spaced-apart, first and second trocar and sleeve assemblies through skin covering the bone and through the bone transversely of the bone tunnel so as to intersect and extend into the portion of a piece of tissue, the trocar in each of the assemblies being disposed within one of the sleeves of the assemblies and substantially filling the sleeve;

removing the trocar from the first of the sleeves, advancing a first rod through the first sleeve and into the portion of a piece of tissue, and then removing the first sleeve, so as to leave the first rod in the bone and the portion of a piece of tissue; and removing the trocar from the second of the sleeves, advancing a second rod through the second sleeve into the portion of a piece of tissue, and then removing the second sleeve, so as to leave the second rod in the bone and the portion of a piece of tissue, whereby to retain the portion of a piece of tissue in the bone tunnel with the rods.

In accordance with a further feature of the invention, there is provided a method for fixing a portion of a piece of tissue in a bone tunnel in a bone, the method comprising the steps of:

advancing first and second spaced-apart drill means through the bone transversely of the bone tunnel so as to intersect and permissibly extend through the bone tunnel;

withdrawing the first and second spaced-apart drill means from the bone tunnel;

locating a portion of a piece of tissue in the bone tunnel in transverse alignment with the paths of the first and second spaced-apart drill means through the bone;

advancing third and fourth spaced-apart drill means into, and permissibly through, the portion of a piece of tissue;

removing the third of the drill means and replacing the third removed drill means with a first rod; and removing the fourth of the drill means and replacing the fourth of the drill means with a second rod;

whereby to retain the portion of a piece of tissue in the bone tunnel with the rods.

BRIEF DESCRIPTION OF THE DRAWINGS

The above and other objects and features of the present invention will be more fully discussed in, or rendered obvious by, the following detailed description of the preferred embodiments of the invention, which is to be considered together with the accompanying drawings wherein like members refer to like parts, and further wherein:

FIG. 12 is a bottom view of a trocar sleeve guide member portion of the rack assembly of FIGS. 10 and 11;

FIG. 13 is a side elevational view of the trocar sleeve guide member;

FIG. 14 is a front elevational view of the trocar sleeve guide member;

FIG. 41 is a side elevational view of a graft ligament, tendon or the like, wherein one end of the graft has been folded back upon itself and tack-stitched in place, and wherein a rod extending through the tissue is shown in phantom;

FIG. 42 is a side elevational view similar to FIG. 41, wherein the graft ligament, tendon or the like has been folded back upon itself, and wherein a rod extending between adjacent folds of the graft is shown in phantom;

FIG. 43 is a side elevational view similar to FIG. 42, wherein the folded tissue has been "whip stitched" together, and wherein a rod extending through the whip stitched tissue mass is shown in phantom;

FIGS. 44–51 are illustrative sectional side elevational views showing the steps of advancing a trocar/trocar sleeve combination into a bone and through a bone tunnel therein, removing the trocar, inserting a rod into the sleeve and across the bone tunnel, removing the sleeve, and pulling an end of a tissue graft around the rod located across the bone tunnel;

FIG. 55 is an illustrative side elevational view of an assembled trocar/trocar sleeve assembly for use in the present invention;

FIGS. 56–63 are illustrative side sectional, elevational views showing the use of long trocars inserted through sleeves, originally placed with the combination depicted in FIG. 55, to penetrate the bone and a bone block for the emplacement of rods to hold the bone block in place within the bone tunnel;

FIG. 64 is a side elevational view of a stepped trocar formed in accordance with the present invention;

FIG. 65 is a side elevational, sectional view showing a trocar sleeve having an internal stop adapted to limit the travel of a stepped trocar, as depicted in FIG. 64, therethrough;

FIG. 66 is an exploded, side sectional, elevational view illustrating the use of a plunger and tapping device for driving a rod through a sleeve in bone and into a bone block located in a bone tunnel;

FIG. 67 is a side elevational view of another trocar/trocar sleeve combination for use in accordance with the present invention;

FIG. 68 is a side elevational view of still another trocar/trocar sleeve combination for use in accordance with the present invention;

FIG. 69 is an illustrative perspective view showing an apertured head substituted for the enlarged cannulated sleeve head depicted in FIG. 19; and FIGS. 70–74 are illustrative side elevational views showing the disposition of a rod across a reduced bone fracture using a trocar/trocar sleeve combination in accordance with the present invention.

DETAILED DESCRIPTION OF THE PREFERRED EMBODIMENTS

Figure 1:
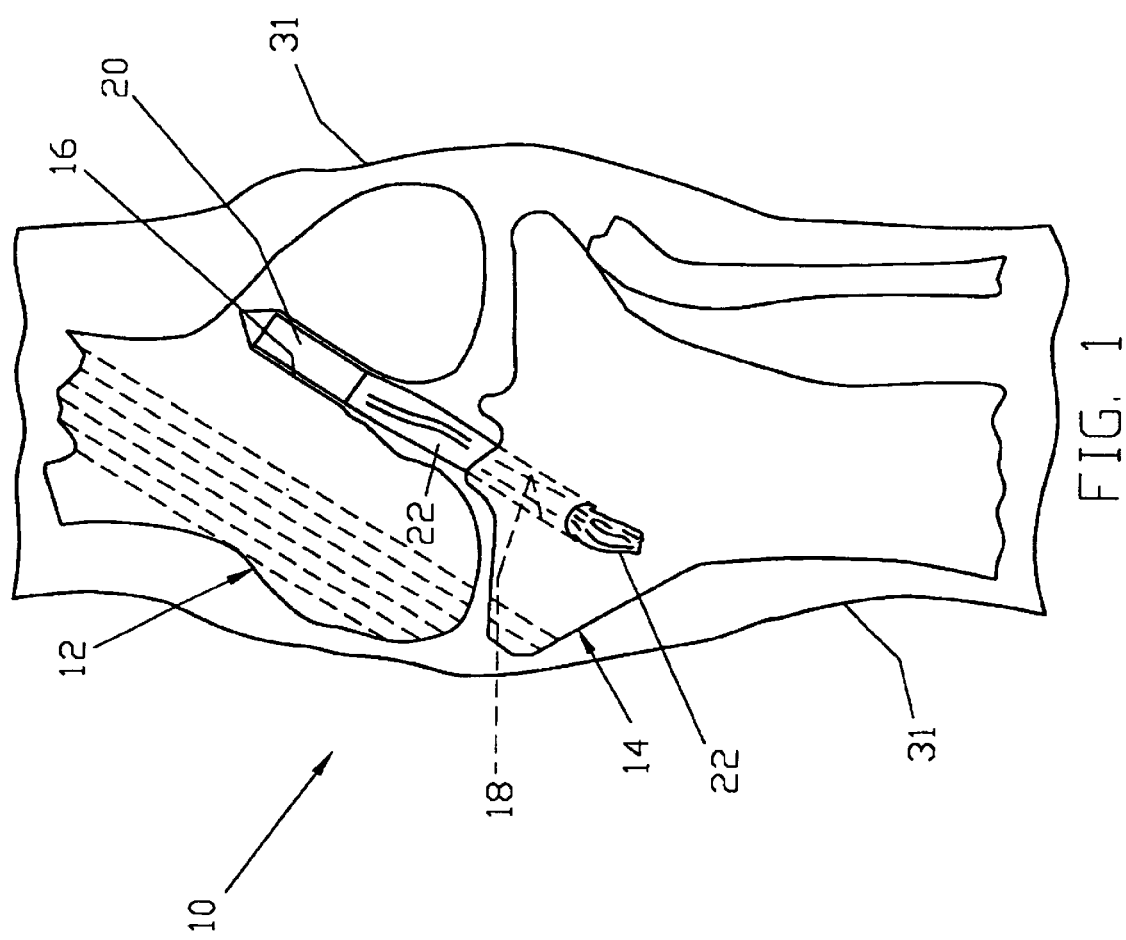
FIG. 1 is a diagrammatical sectional view of a human knee joint, with appropriate bone tunnels formed therein and with a ligament bone block disposed in one of the tunnels.

Referring first to FIG. 1, it will be seen that a human knee joint 10, including a femur 12 and tibia 14, has been provided with an appropriate femoral bone tunnel 16 and an appropriate tibial bone tunnel 18. Such tunnels may be provided in ways well known in the art. A bone block 20, having ligament material 22 attached thereto, has been positioned in femoral tunnel 16. Such bone block positioning may also be achieved in ways well known in the art.

Figure 2:
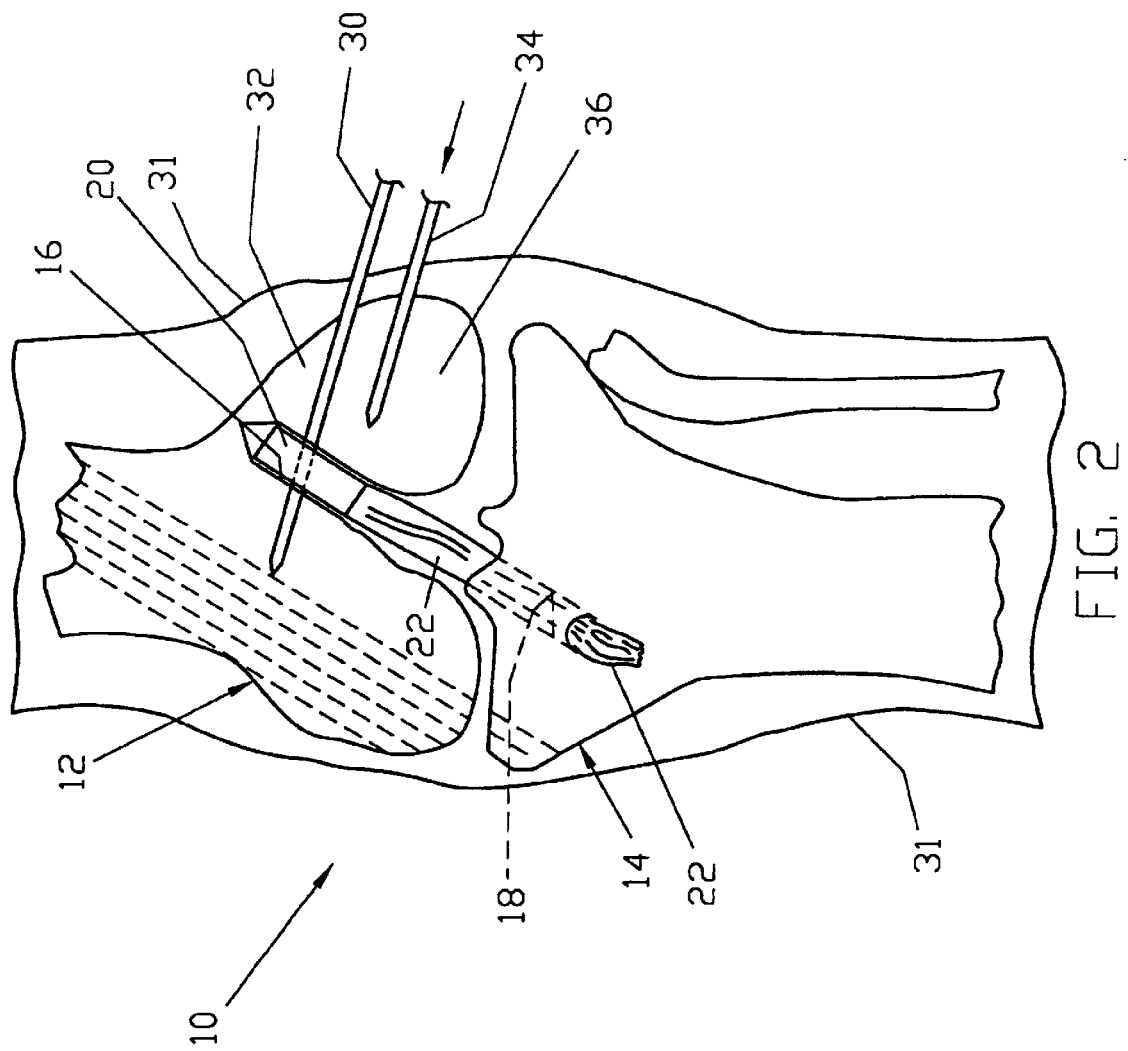
FIG. 2 is similar to FIG. 1, but illustrative of a metal wire insertion phase of the inventive method.
Figure 3:
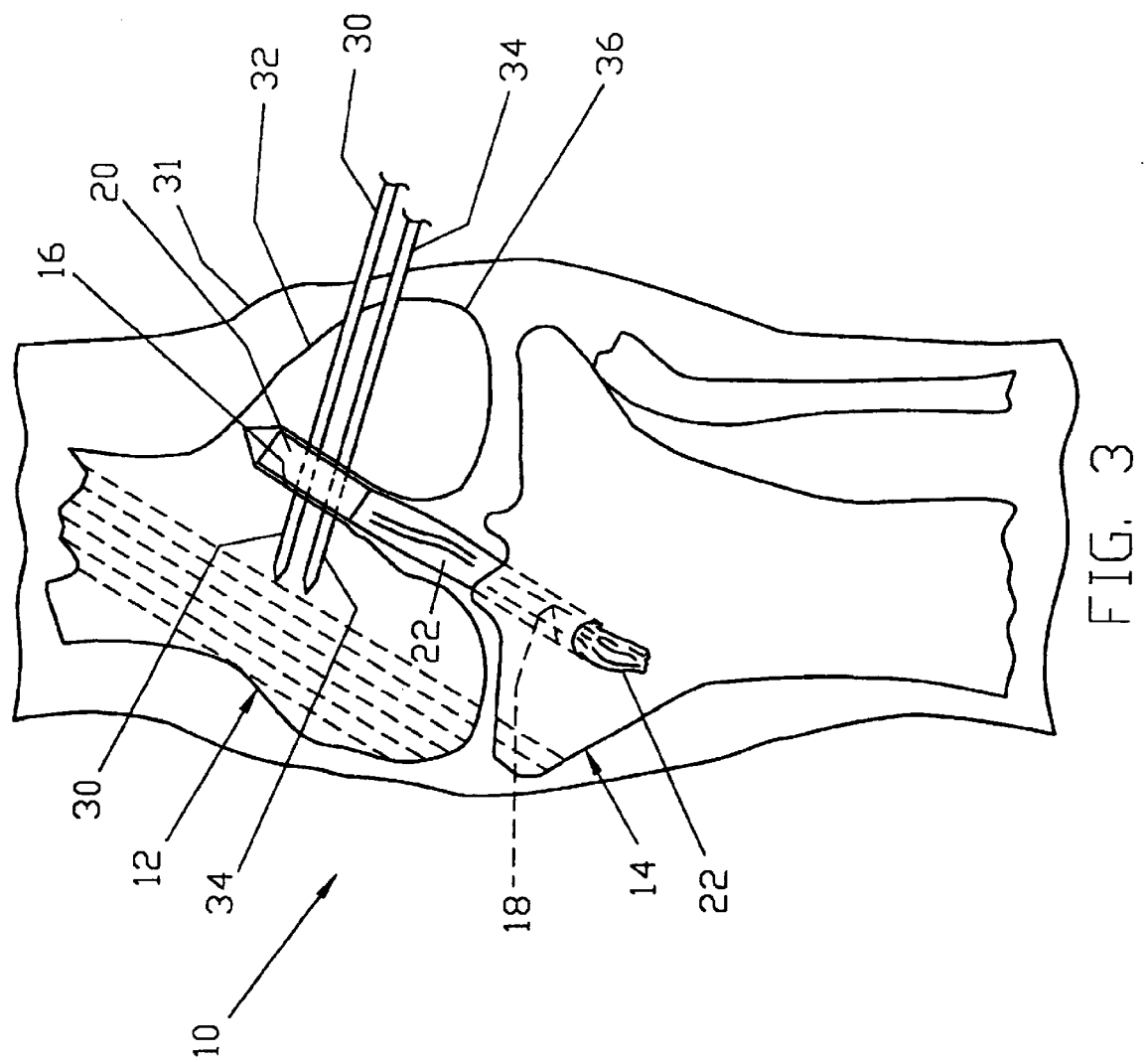
FIG. 3 is similar to FIG. 2 but illustrative of completion of the metal wire insertion phase.

Looking next at FIG. 2, in accordance with the present invention, a first metal wire 30, which may be of the type commonly referred to as a guidewire or a "K-wire", is advanced through skin 31 and a first portion 32 of femur 12. First wire 30 is advanced transversely of femoral tunnel 16 so as to intersect and extend through bone block 20, as shown in FIG. 2. Thereafter, or simultaneously therewith, a second metal wire 34 is advanced through a second portion 36 of femur 12. Second wire 34 is also advanced transversely of femoral tunnel 16 so as to also intersect and extend through bone block 20 (FIG. 3). At this point, bone block 20 is securely held in femoral tunnel 16 by the two spaced-apart metal wires 30, 34.

Figure 4:
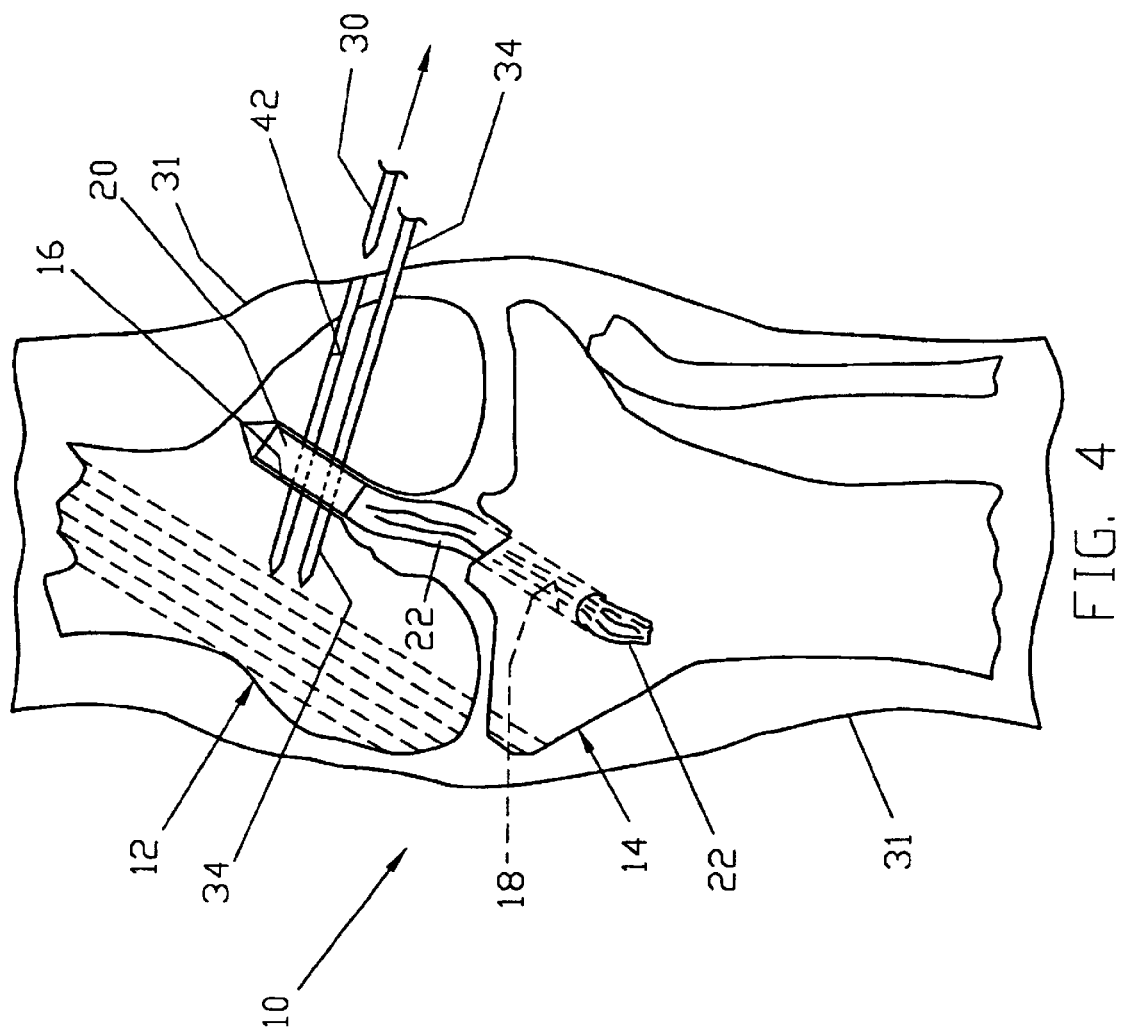
FIG. 4 is similar to FIG. 3, but illustrative of a first metal wire withdrawal phase.
Figure 5:
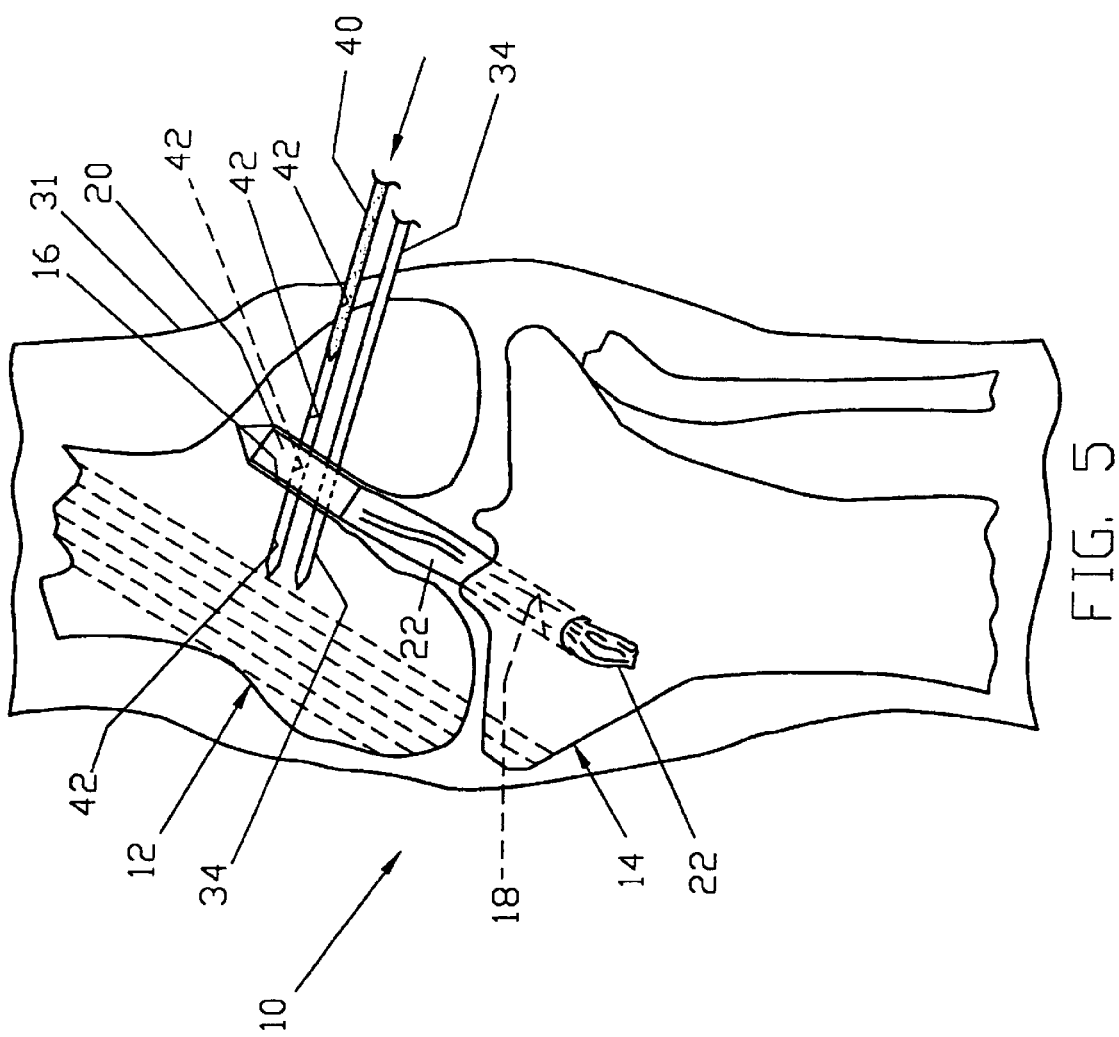
FIG. 5 is similar to FIG. 4, but illustrative of a first absorbable rod insertion phase.
Figure 6:
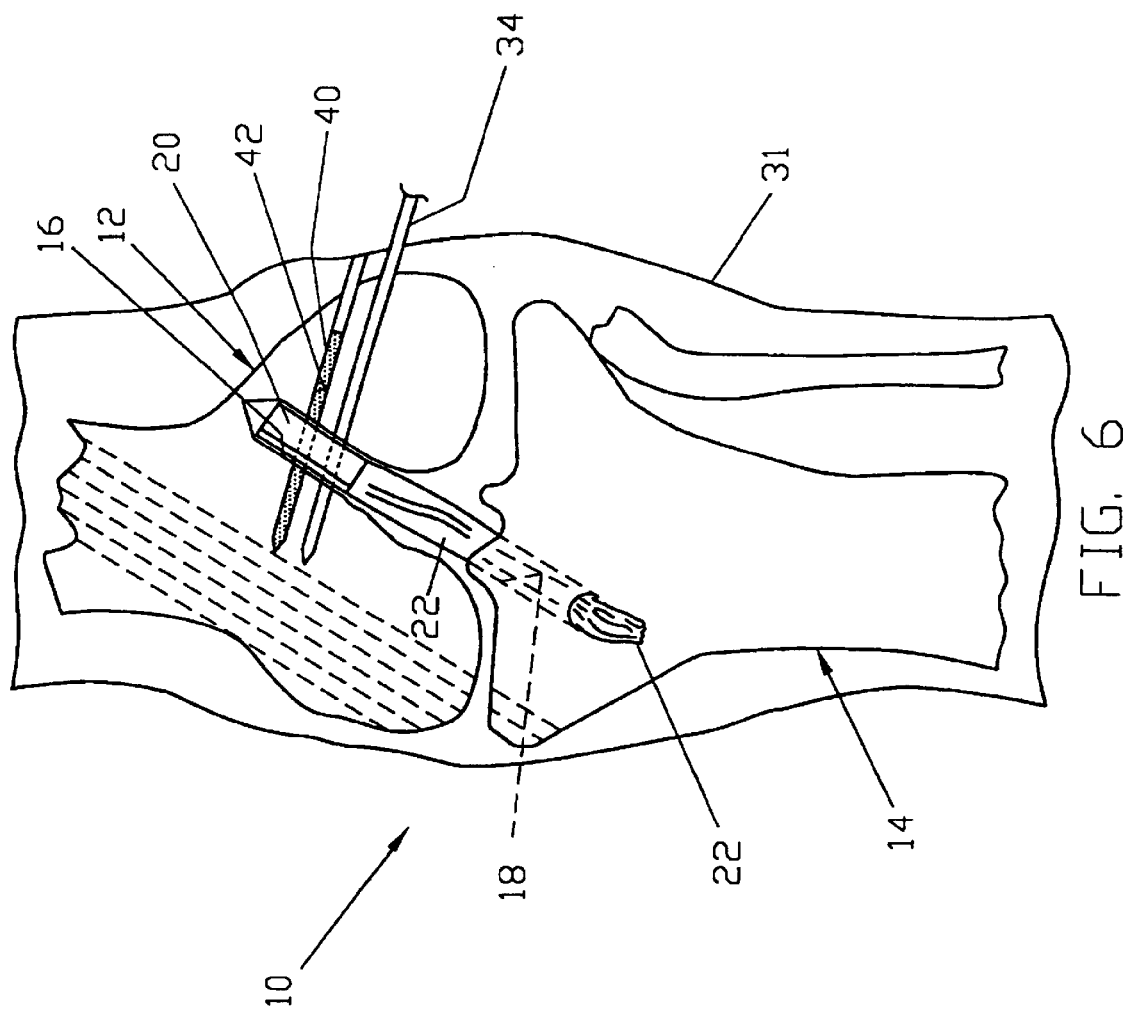
FIG. 6 is similar to FIG. 5, but illustrative of the first absorbable rod having been fully inserted.

Referring next to FIG. 4, it will be seen that one of the two wires 30, 34 is then removed, while the other of the two wires 30, 34 is left in place in femur 12 and bone block 20. By way of example but not limitation, wire 30 may be removed while wire 34 is left in place. A first absorbable rod 40 (FIG. 5) is then advanced through the bore 42 left by the removal of first wire 30, such that first absorbable rod 40 extends through femur 12 and bone block 20 (FIG. 6). At this point, bone block 20 is securely held in femoral tunnel 16 by both metal wire 34 and first absorbable rod 40.

Figure 7:
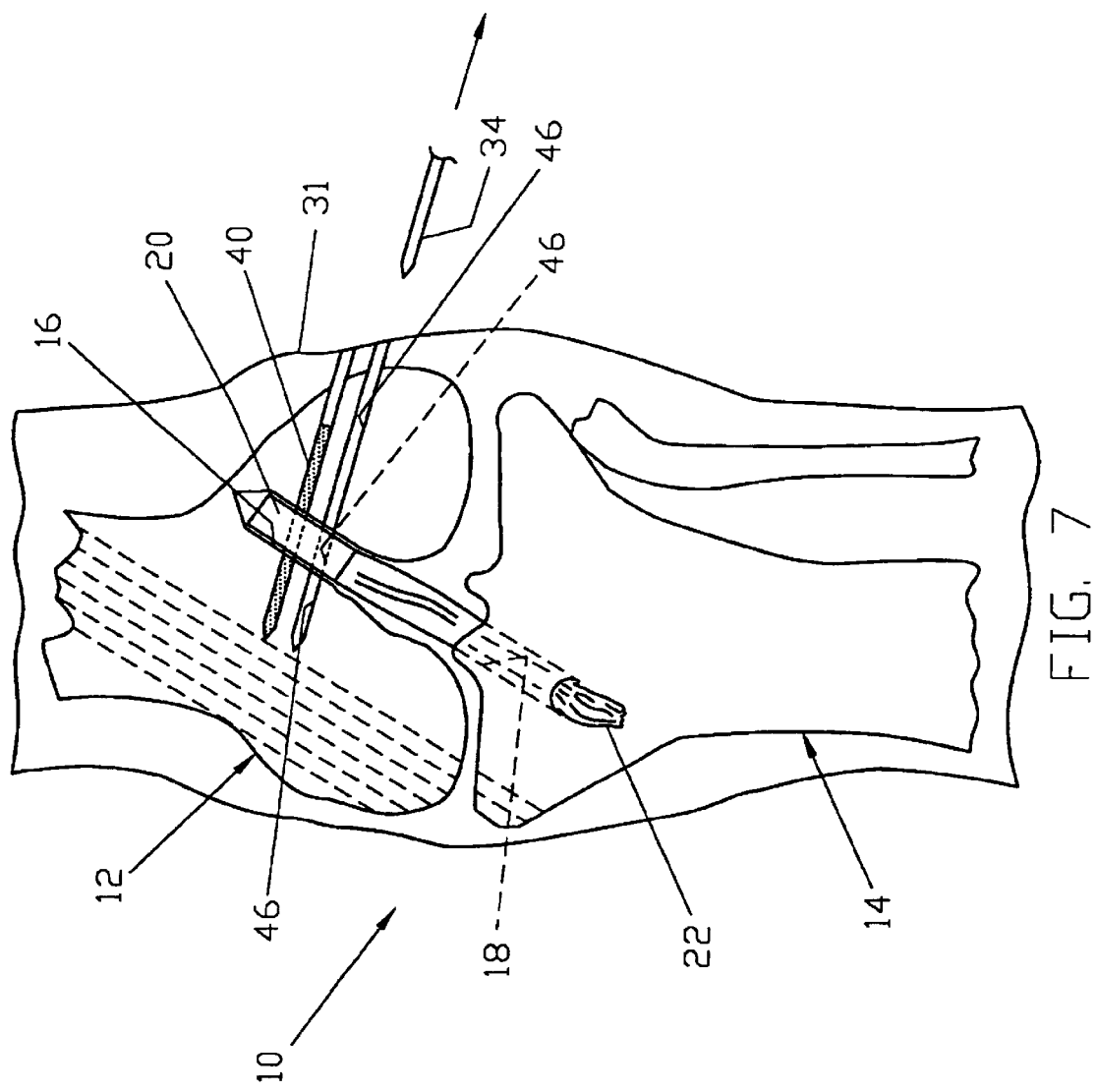
FIG. 7 is similar to FIG. 6, but illustrative of a second metal wire withdrawal phase.
Figure 8:
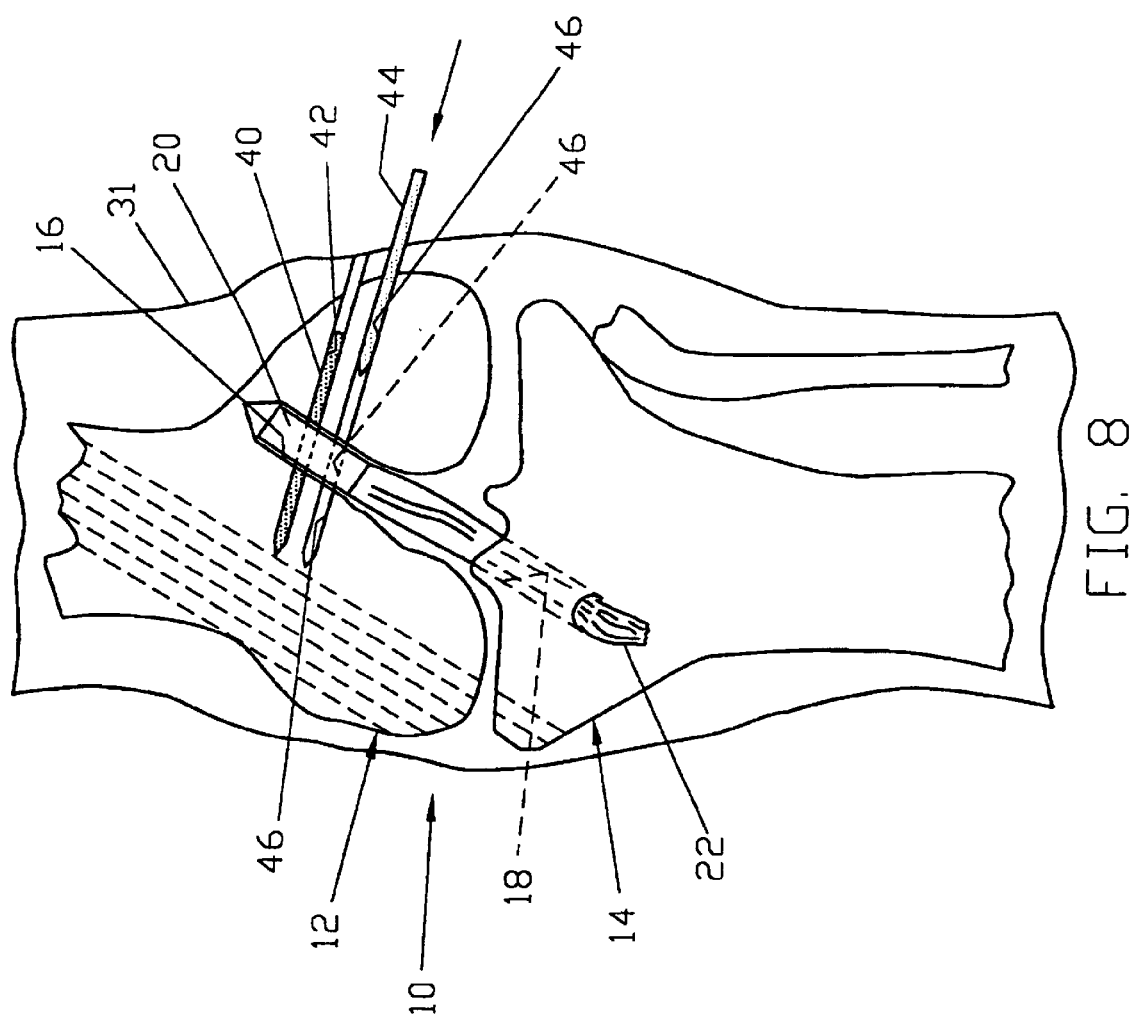
FIG. 8 is similar to FIG. 7, but illustrative of a second absorbable rod insertion phase.
Figure 9:
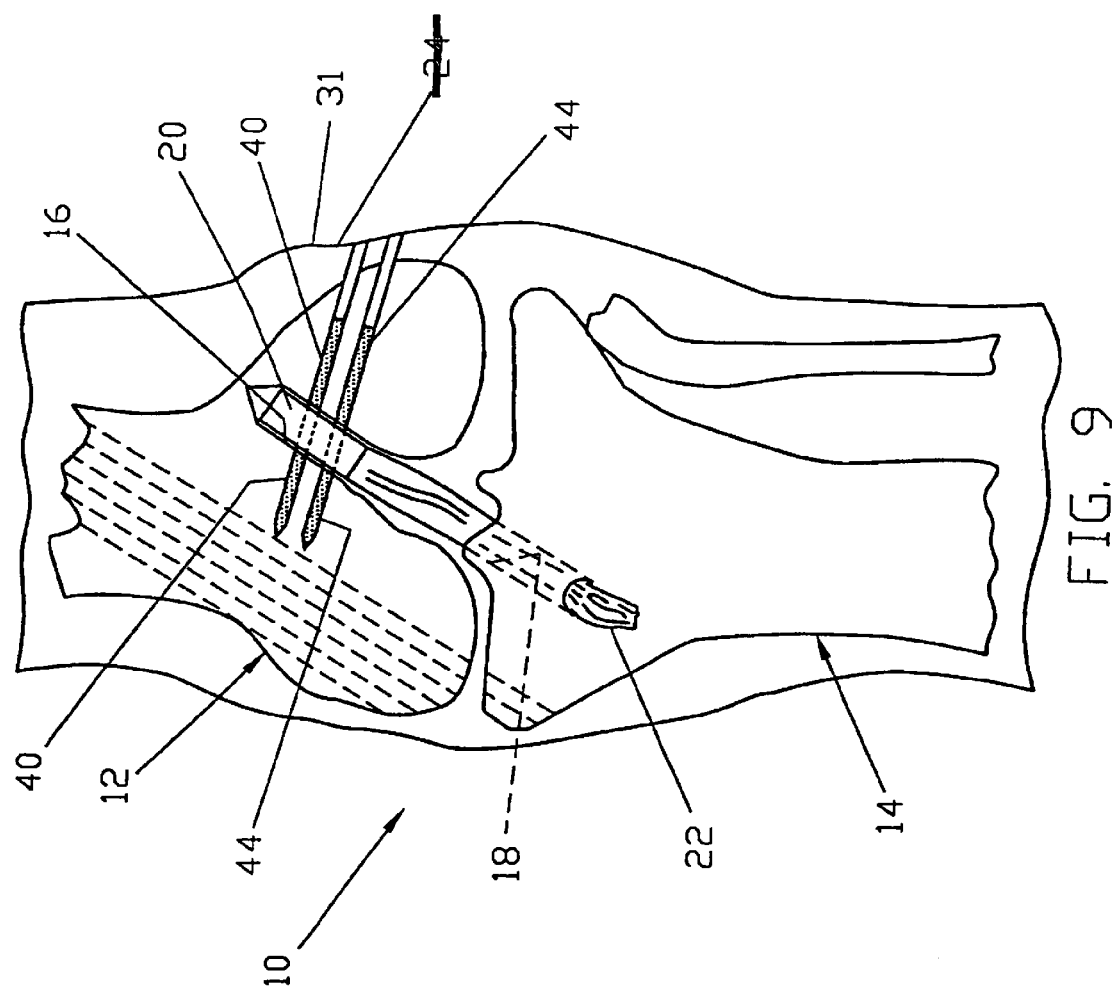
FIG. 9 is similar to FIG. 8, but illustrative of the completion of the absorbable rod insertion phase of the inventive method.
Figure 10:
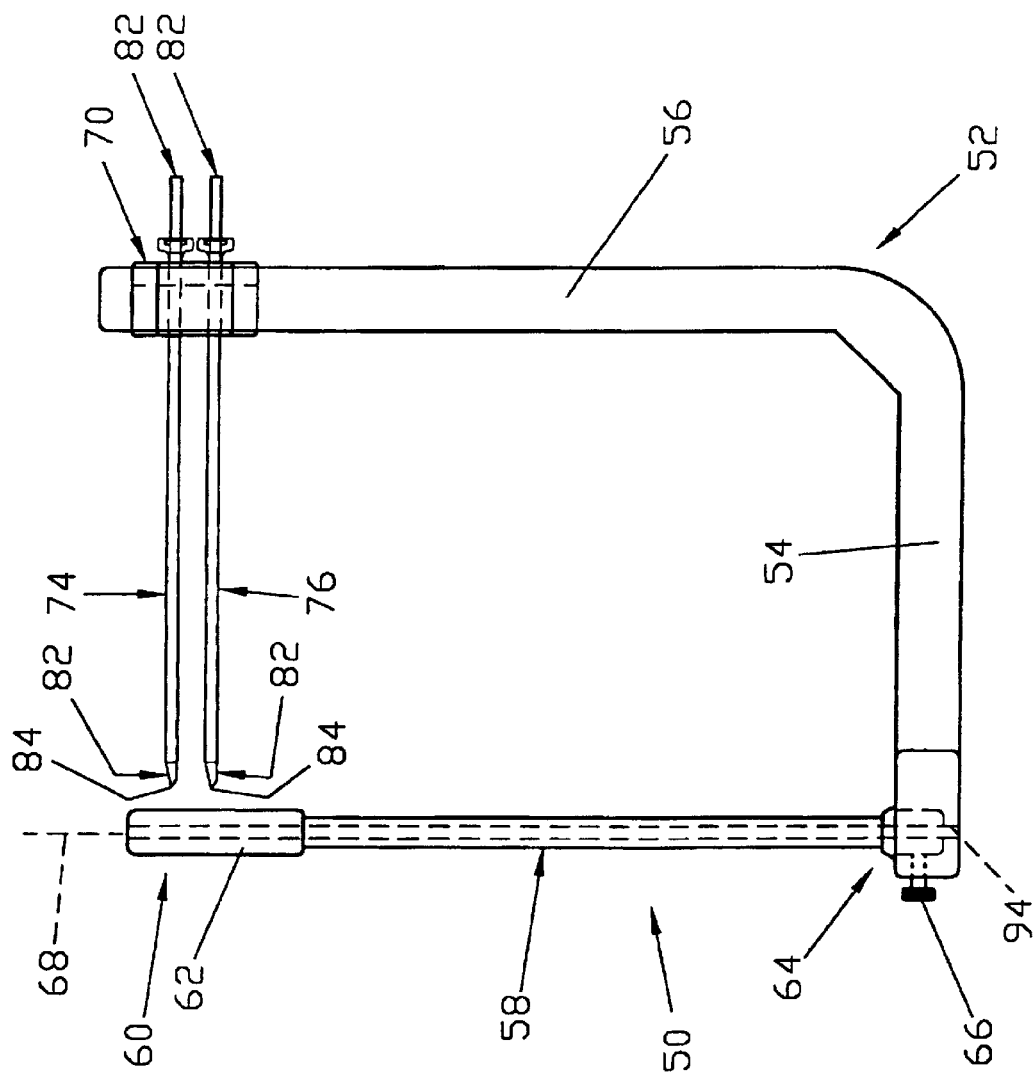
FIG. 10 is a side elevational view of one form of rack assembly for cross-pinning a bone block in a bone tunnel in accordance with an embodiment of the invention.

Thereafter, the other of the two metal wires 30, 34 is withdrawn (e.g., in FIG. 7, metal wire 34 is removed), and a second absorbable rod 44 (FIG. 8) is advanced through the bore 46 left by the removal of metal wire 34, such that second absorbable rod 44 also extends through femur 12 and bone block 20 (FIG. 9).

It will be appreciated that, upon completion of the insertion of second absorbable rod 44 (FIG. 9), bone block 20 is retained in femoral tunnel 16 solely by the absorbable rods 40, 44.

The absorbable rods 40, 44 may be made out of a material such as polylactic acid (PLA), polyglycolic acid (PGA), polydiaxanone (PDS), or out of some other such material which is formable into a relatively rigid and hard configuration, but which is absorbable by the body of the patient over time. If desired, the distal ends of absorbable rods 40, 44 can be pointed or rounded so as to facilitate their deployment into the body.

There is thus provided a method by which a bone block is fixed within a bone tunnel, such that the bone block is anchored in the tunnel by cross-pins which are made out of a material which is absorbable by the body over time.

It will be understood that while the above method has been described and illustrated with respect to first and second wires replaced serially by first and second absorbable rods, the method may be exercised with any reasonable number of wires, exceeding one. In the latter instance, the method includes the steps of placing the bone block in the bone tunnel, and then advancing a plurality of metal wires through the bone, transversely of the tunnel, so as to intercept the bone block and extend therethrough. At least one of the wires is then removed while leaving at least one of the wires in place, and that at least one removed wire is then replaced by at least one absorbable rod. At least one further of the wires is then removed and that at least one removed wire is then replaced by at least one further absorbable rod. The last-mentioned step is then repeated until a selected number of the metal wires is each replaced with an absorbable rod, whereby to retain the bone block in the bone tunnel with absorbable rods.

It will also be understood that while FIGS. 1–9 show metal wires 30, 34 and absorbable rods 40, 44 passing completely through bone block 20 during the cross-pinning procedure, it is also possible for metal wires 30, 34 and absorbable rods 40, 44 to pass only part way across bone block 20, if the same should be desired.

Furthermore, it will also be understood that while the above method has been described and illustrated with respect to metal wires 30, 34 being used to drill through femur 12 and bone block 20, other drilling implements (e.g., a twist drill or a spade drill) might also be used.

As noted above, various drill guides have been developed for forming transverse passages through the femur and bone block so as to cross-pin the bone block within the femoral tunnel. If desired, the inventive method of the present invention may be practiced using such known drill guides. Alternatively, the present invention may also be practiced using a novel rack assembly.

More particularly, and looking now at FIGS. 10–17, a novel rack assembly 50 is disclosed for practicing the present invention. Rack assembly 50 comprises an L-shaped member 52 having a base portion 54 and an arm portion 56.

The arm portion 56 extends transversely, and preferably is normal to, base portion 54.

Rack assembly 50 also includes a cannulated sleeve 58 which, at a first end 60 thereof, is provided with an enlarged head portion 62, and which, at a second end 64 thereof, is releasably connectable to base portion 54 of L-shaped member 52. Sleeve 58 may be retained in a bore 65 (FIG. 11) formed in base portion 54 by a set screw 66.

A trocar sleeve guide member 70 is removably connectable to arm portion 56 of L-shaped member 52. Trocar sleeve guide member 70 is provided with bores 72 extending therethrough. Bores 72 extend substantially normal to a longitudinal axis 68 (FIG. 10) of the enlarged head portion 62 of cannulated sleeve 58. A set screw 71 (FIG. 11) may be used to releasably retain trocar sleeve guide member 70 in position on arm portion 56. Alternatively, or in addition, arm portion 56 may be provided with stop means (not shown) for limiting the movement of the trocar sleeve guide member 70 along arm portion 56. Trocar sleeve guide member 70 is preferably formed in two halves releasably held together by a set screw 73 (FIG. 11), whereby trocar sleeve guide member 70 can be slidably mounted on, or detached from, trocar sleeves 74, 76 passing through bores 72, as will hereinafter be discussed.

Figure 16:
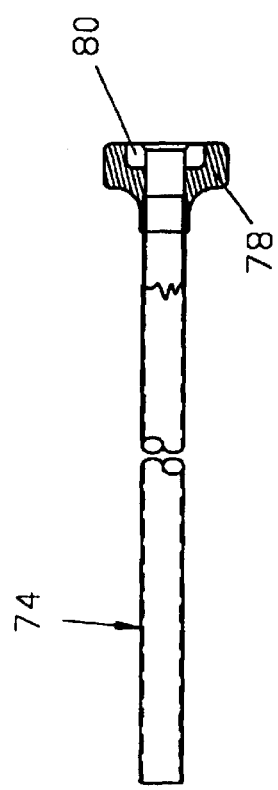
FIG. 16 is an interrupted side elevational view, broken away and partly in section, of a trocar sleeve portion of the rack assembly of FIG. 10.
Figure 17:
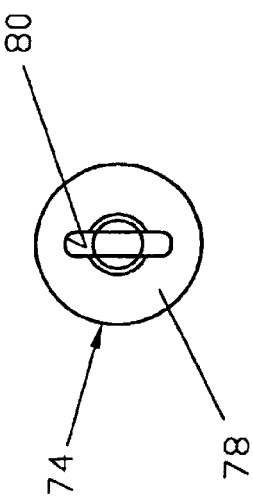
FIG. 17 is an end view of the trocar sleeve portion of FIG. 16.

First and second trocar sleeves 74, 76 are slidably received by bores 72, such that sleeves 74, 76 are axially and rotatably movable in bores 72. Referring to FIGS. 16 and 17, it will be seen that trocar sleeve 74 is provided with a collar portion 78 having a slot 80 formed therein. Sleeve 76 is substantially identical to sleeve 74.

Rack assembly 50 also includes one or more trocars 82 (FIGS. 10 and 15) for disposition in the sleeves 74, 76. Each trocar 82 is provided with a sharp end 84 (FIG. 15) for penetration of bone. A transversely-extending pin 86 is provided near (but spaced from) the opposite end of the trocar 82. Pin 86 is fixed in place and is receivable by the slots 80 of trocar sleeves 74, 76 such that axial (in a distal direction) and rotational movement of trocar 82 causes similar movement of sleeves 74, 76.

The first and second absorbable rods 40, 44 are slidable through sleeves 74, 76, as will be further described hereinbelow.

FIGS. 18–28 illustrate how rack assembly 50 may be used to practice the present invention.

Figure 18:
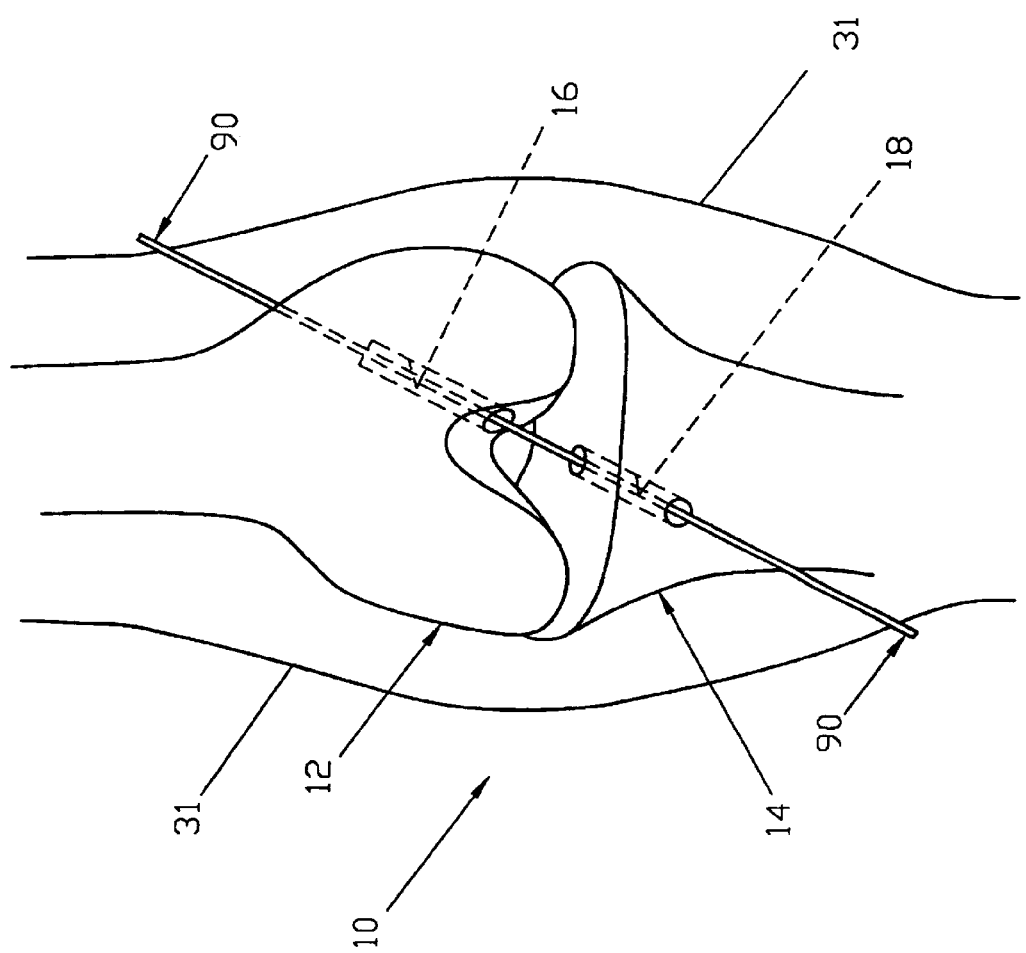
FIG. 18 is a diagrammatical view of a human knee joint and illustrative of a step in a method in which the rack assembly of FIG. 10 is used.

Referring now to FIG. 18, there is shown a human knee joint 10 including femur 12 and tibia 14. An appropriate femoral tunnel 16 and an appropriate tibial tunnel 18 have been provided, as by means and methods well known in the art. A guidewire 90 extends through the bone tunnels 16, 18 as shown.

Figure 11:
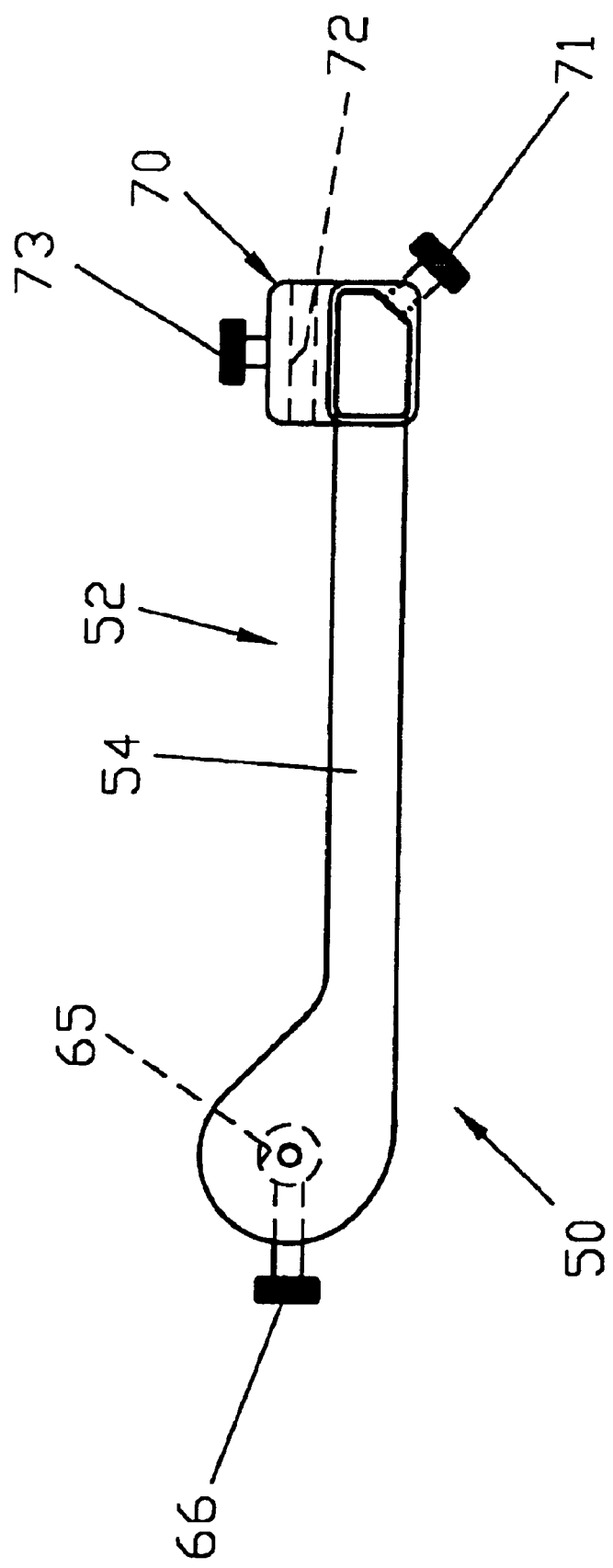
FIG. 11 is a bottom view of the rack assembly of FIG. 10.
Figure 15:
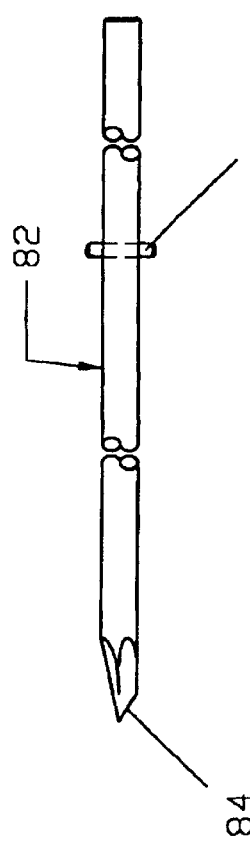
FIG. 15 is an interrupted side elevational view of a trocar portion of the rack assembly of FIG. 10.
Figure 19:
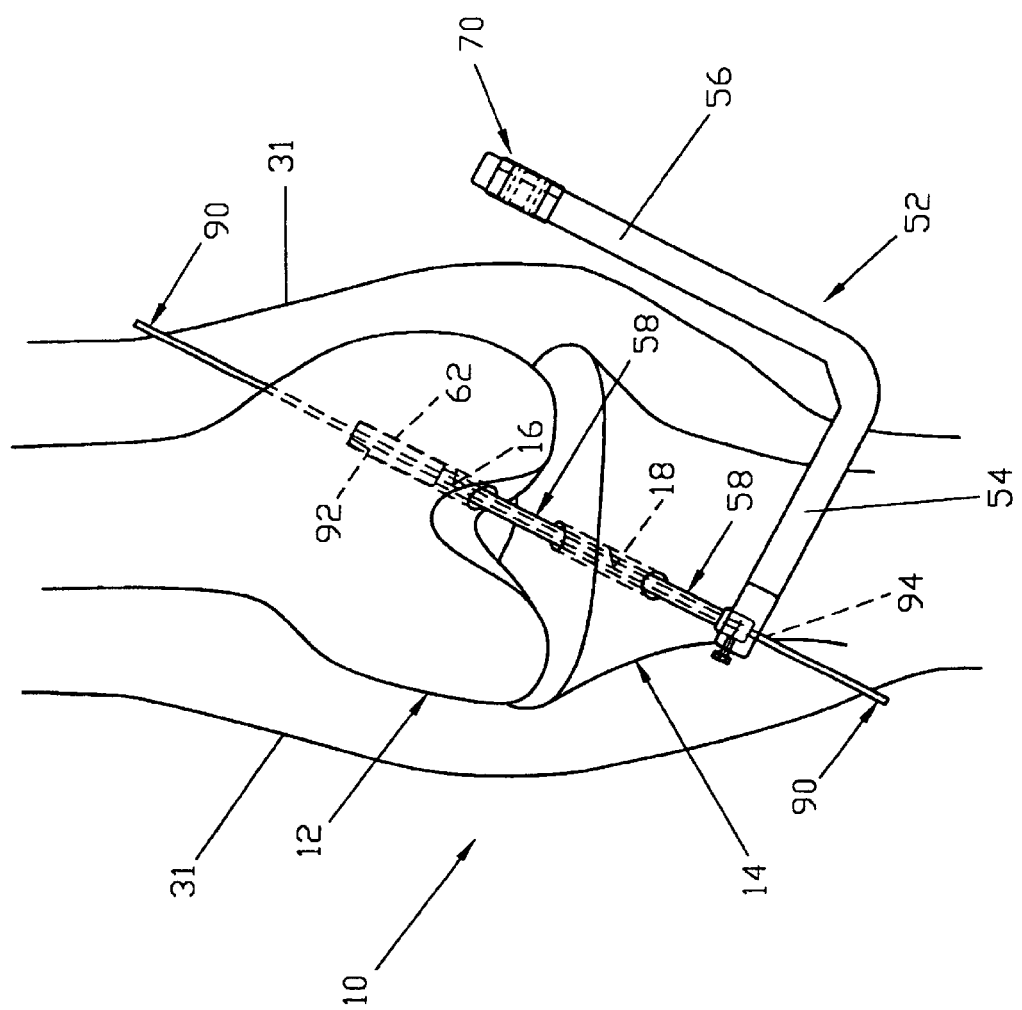
FIGS. 19–28 are diagrammatical views illustrating a series of steps in the use of the rack assembly of FIG. 10.

In accordance with the present invention, the rack assembly's cannulated sleeve 58 is fed over guidewire 90, through tibial tunnel 18 and into femoral tunnel 16, until the cannulated sleeve's head portion 62 engages an annular shoulder 92 in femoral tunnel 16 (FIG. 19). As this occurs, guidewire 90 extends through a bore 94 (FIGS. 10 and 19) formed in base portion 54 of L-shaped member 52. The cannulated sleeve's head portion 62 is preferably sized so as to form a snug fit in femoral tunnel 16. Cannulated sleeve 58 may be positioned in the bone tunnels 16, 18 and then connected to L-shaped member 52 or, more preferably, cannulated sleeve 58 may be first connected to L-shaped member 52 and then positioned in femur 12 and tibia 14. Trocar sleeve guide member 70, if not already positioned on arm portion 56, is then fixed to arm portion 56, as by set screw 71 (FIG. 11).

Figure 20:
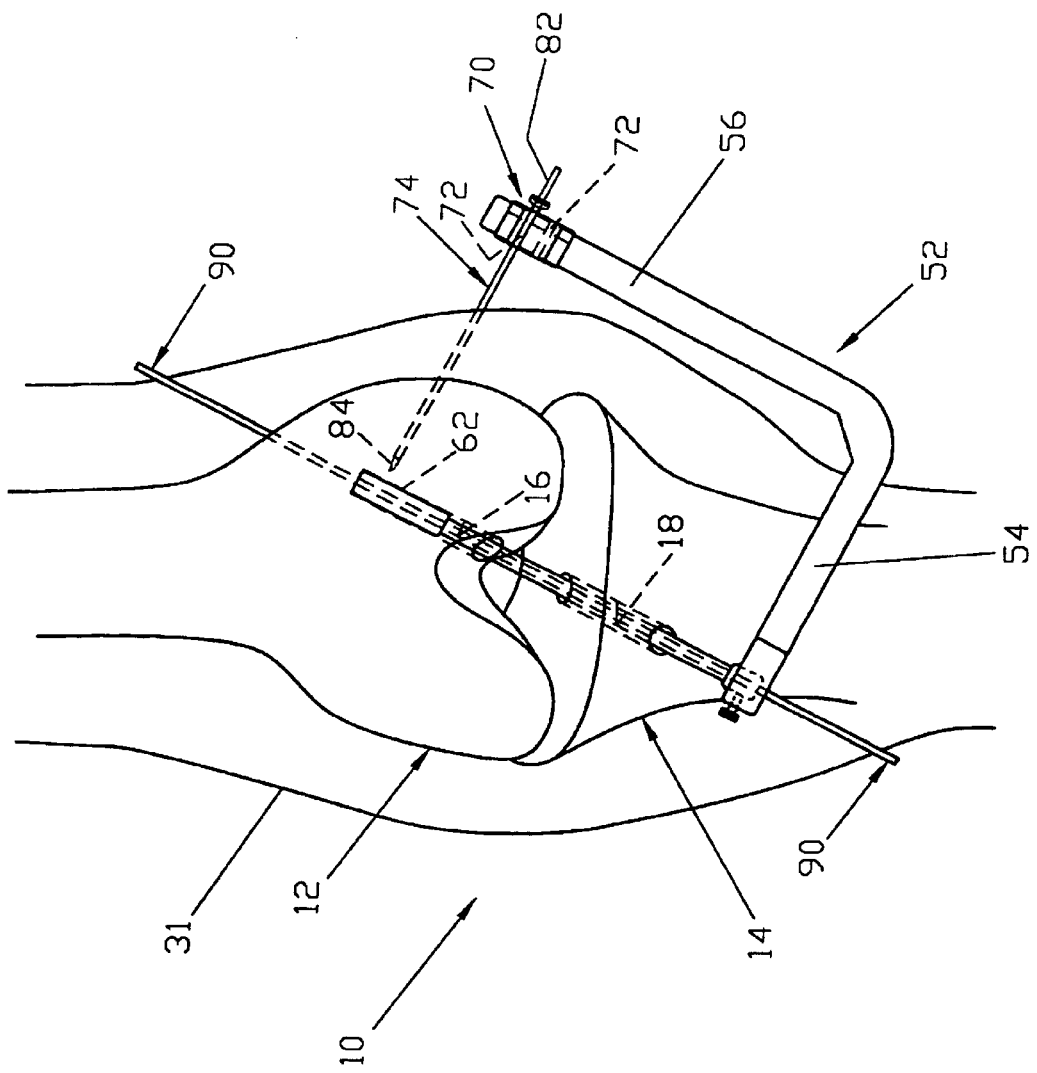

First trocar sleeve 74 is then inserted in a bore 72 of guide member 70 (FIG. 20), and trocar 82 is extended through sleeve 74 until pin 86 (FIG. 15) of trocar 82 is nested in slot 80 (FIGS. 16 and 17) of sleeve 74, with the trocar's sharp end 84 extending beyond the distal end of sleeve 74 (FIG. 20). Alternatively, trocar 82 may be mounted in first trocar sleeve 74 before first trocar sleeve 74 is mounted in a bore 72. The combination of trocar sleeve 74 and trocar 82 is then drilled, as a unit, into femur 12 toward, but short of, the enlarged head portion 62 of cannulated sleeve 58 (FIG. 20).

Figure 21:
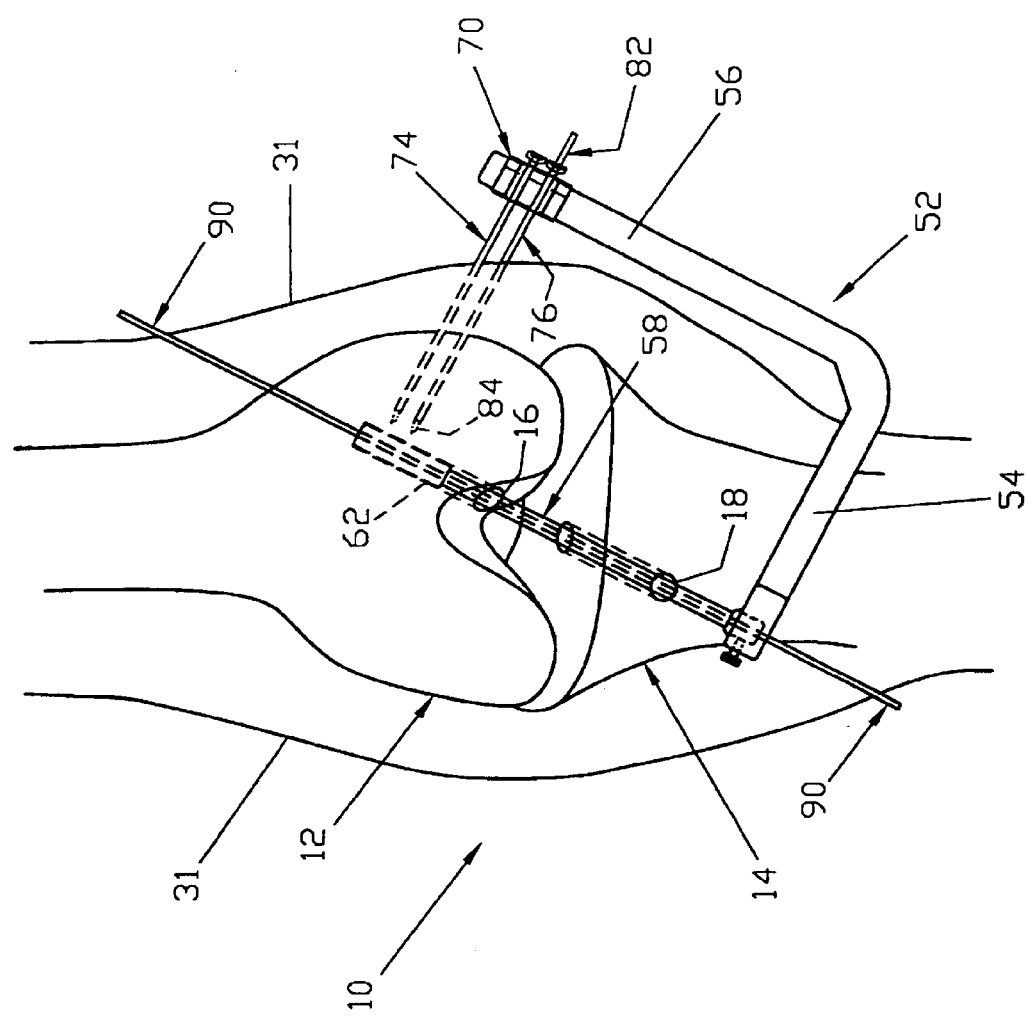
Figure 22:
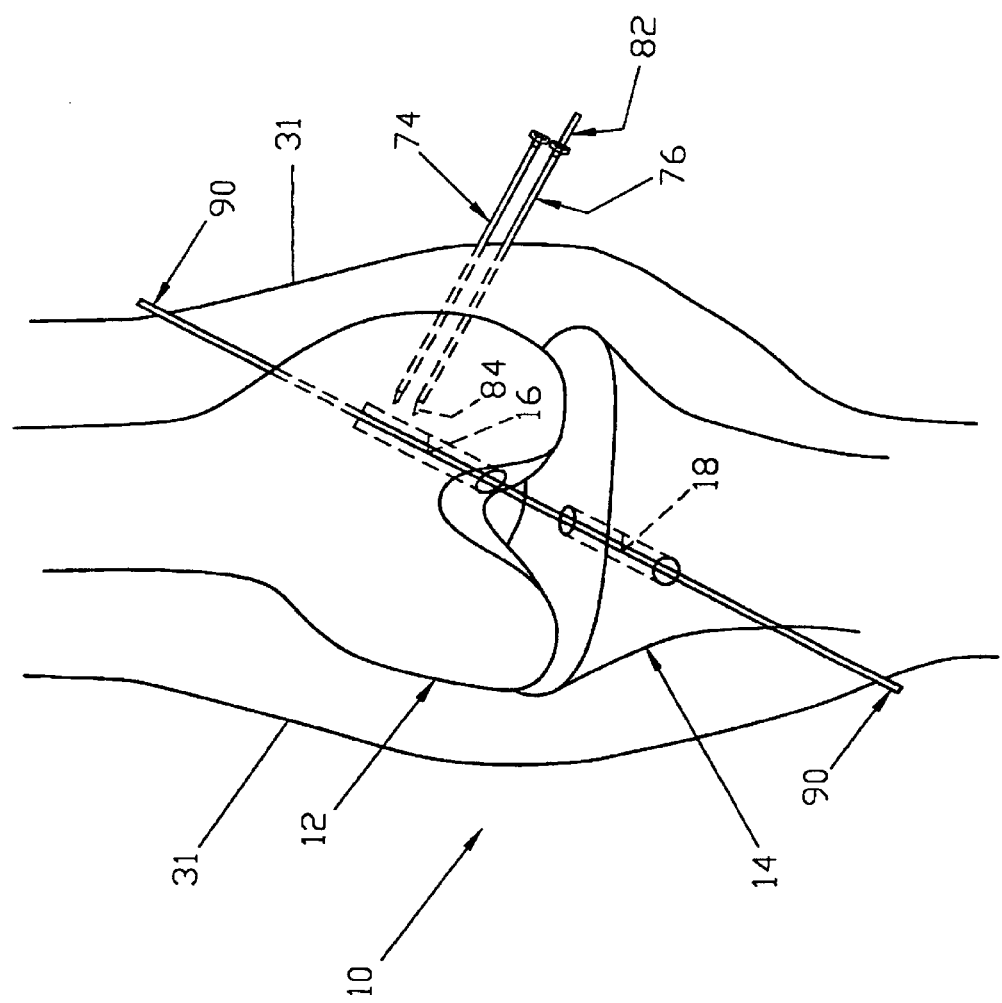

Trocar 82 may then be withdrawn from first trocar sleeve 74 and placed in second trocar sleeve 76 (FIG. 21). Alternatively, a second trocar 82 may be provided for second trocar sleeve 76. In either case, the combination of trocar sleeve 76 and trocar 82 is then drilled, as a unit, into femur 12 toward, but short of, head portion 62 of cannulated sleeve 58. The rack's L-shaped member 52 may then be removed from the surgical site. This may be accomplished by first loosening set screw 73 (FIG. 11) so as to separate trocar sleeve guide member 70 into its two halves, whereby trocar sleeves 74, 76 will be freed from guide member 70, and then sliding cannulated sleeve 58 downward along guidewire 90 until the cannulated sleeve emerges from bone tunnels 16, 18. This procedure will leave trocar sleeves 74, 76 lodged in femur 12 (FIG. 22).

Figure 23:
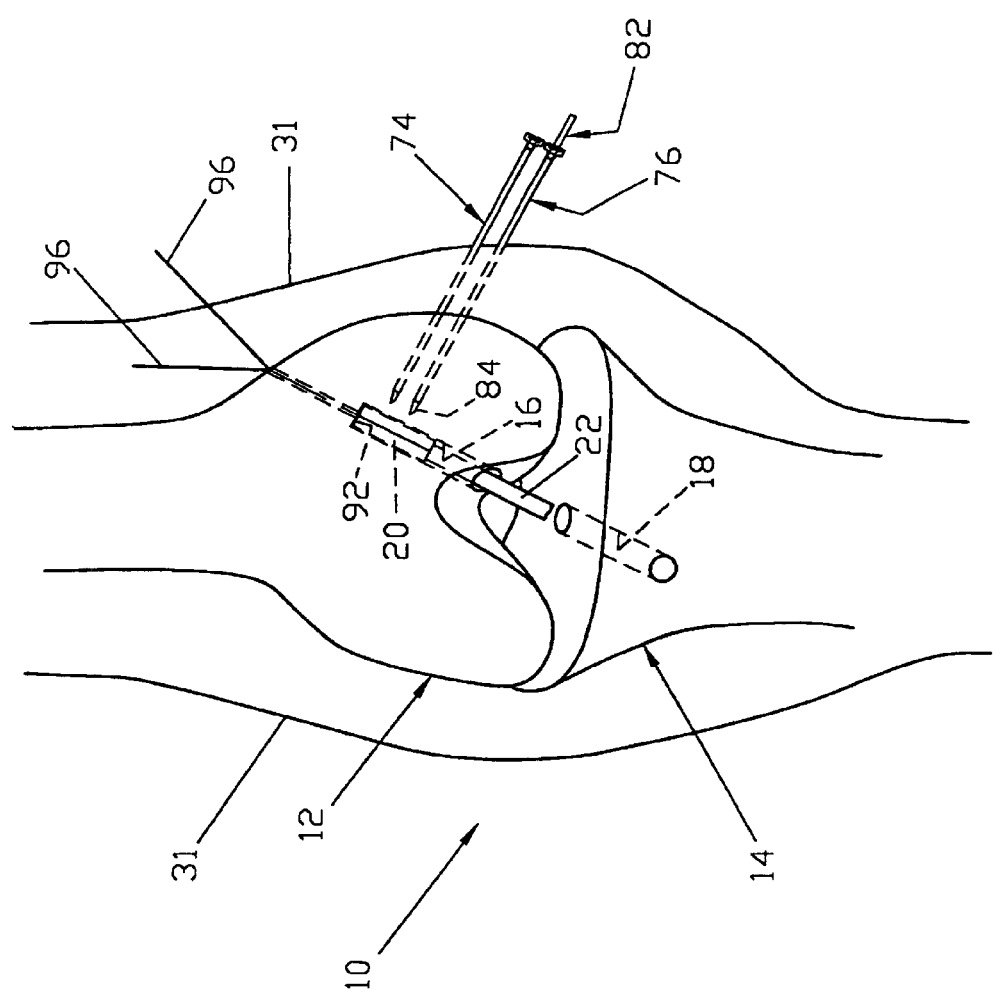

Guidewire 90 is then used to pull a suture 96, which is attached to bone block 20, up through tibial tunnel 18 and into femoral tunnel 16, until bone block 20 engages the annular shoulder 92 in femoral tunnel 16 (FIG. 23). Guidewire 90 may be provided with an eyelet (not shown) adjacent to its proximal end so as to facilitate this procedure. Bone block 20 can then be held is this position by maintaining tension on the portion of suture 96 emerging from the top of femur 12.

Figure 24:
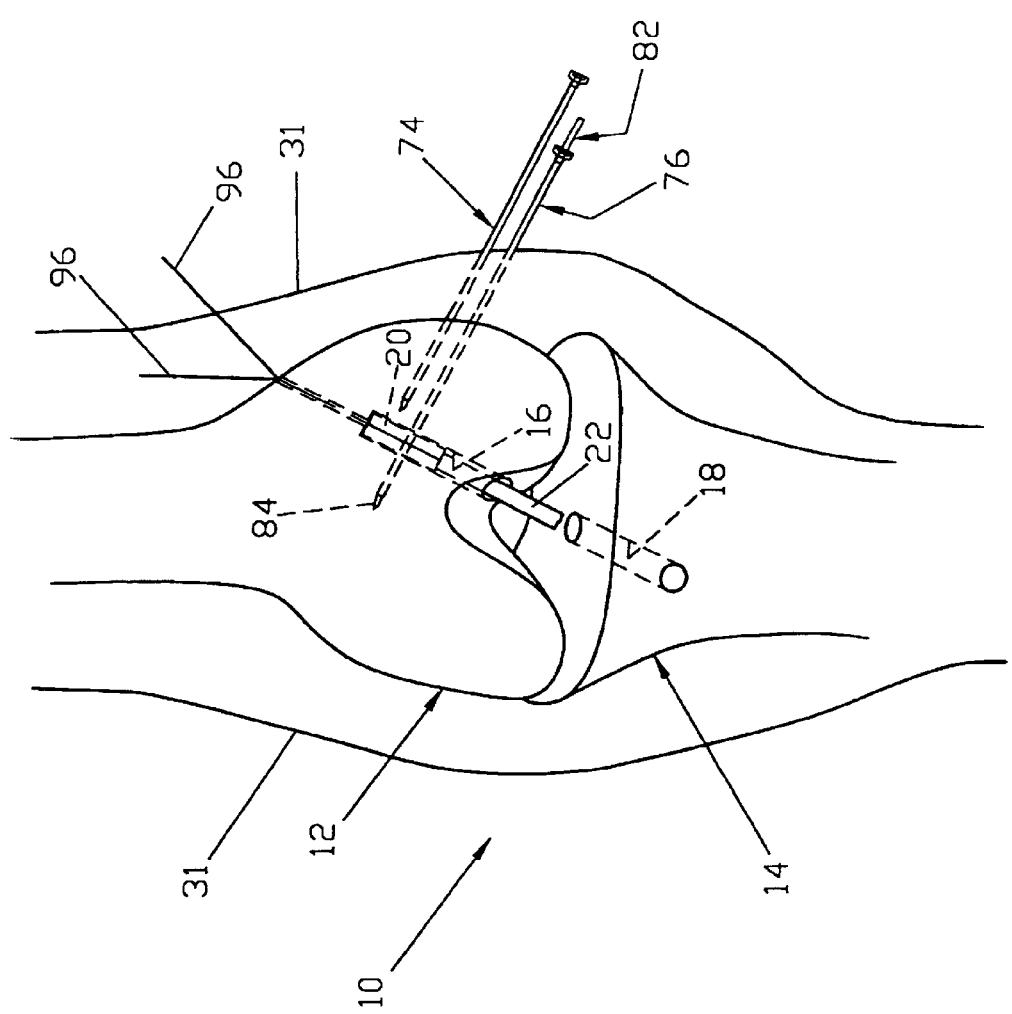
Figure 25:
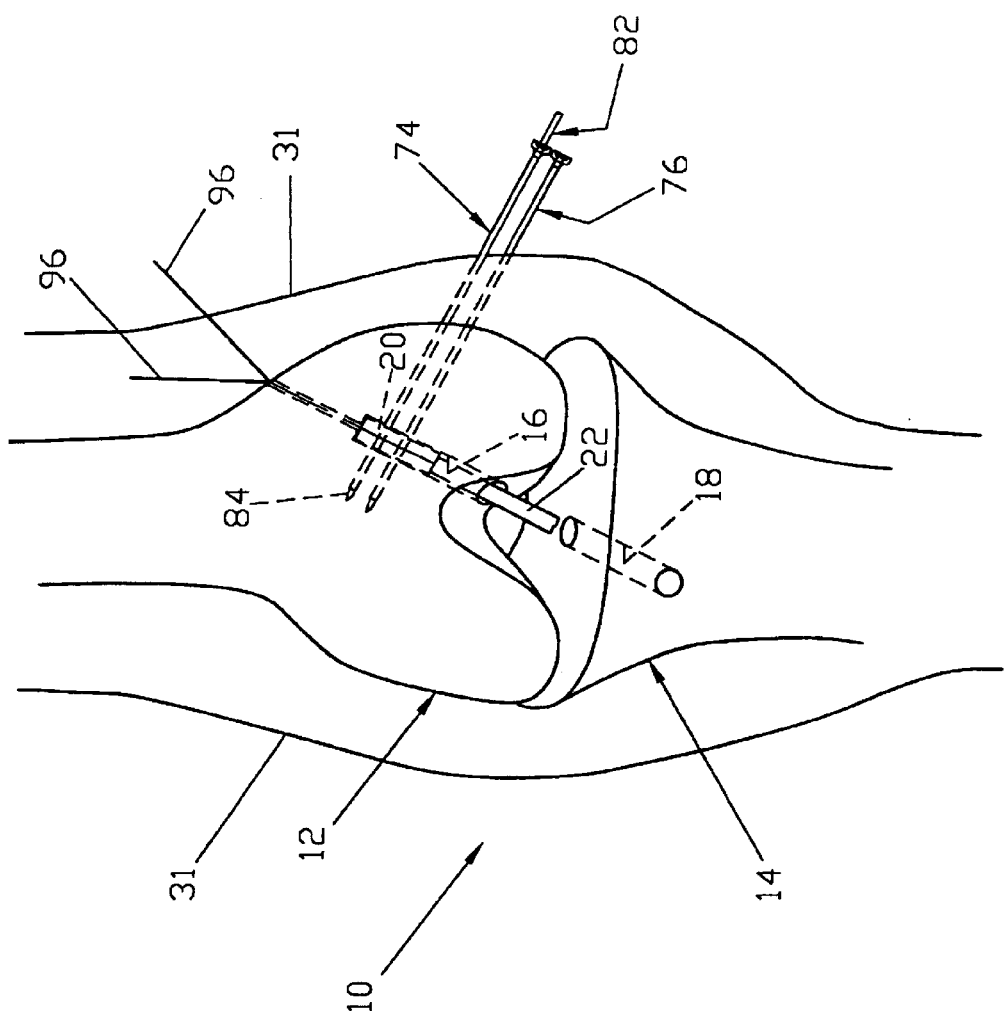
Figure 26:
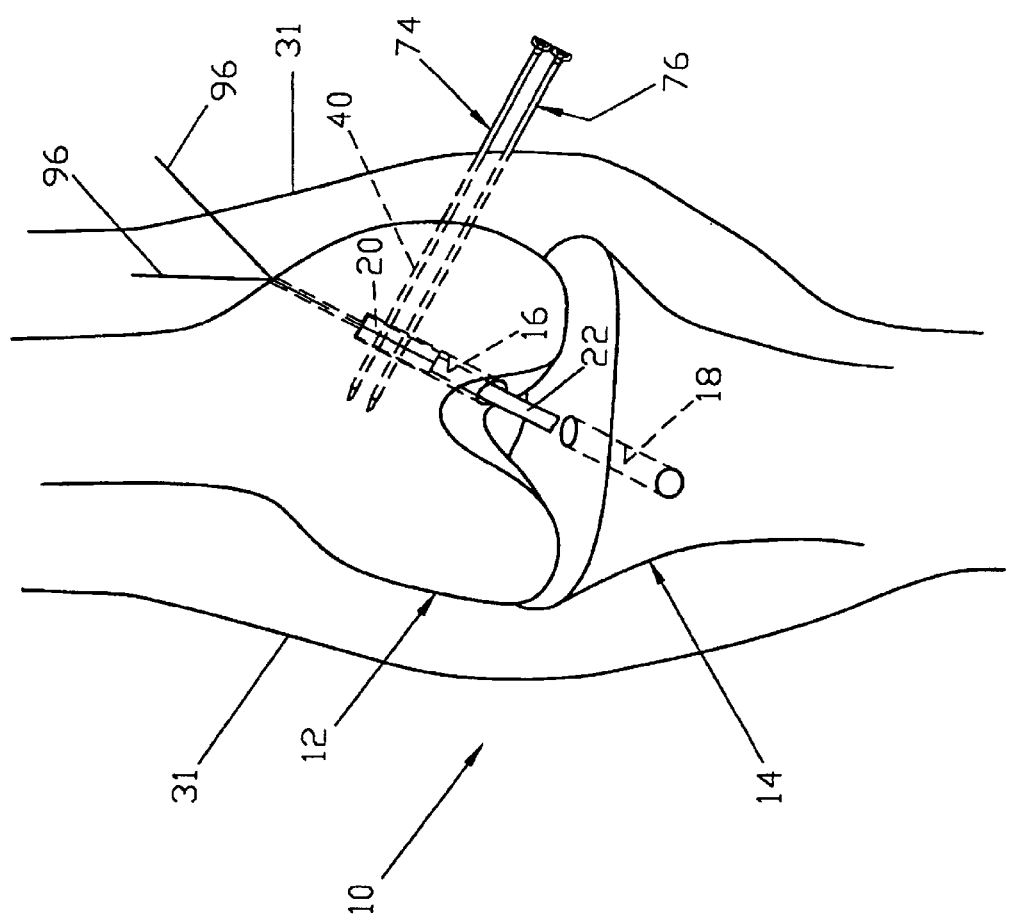
Figure 27:
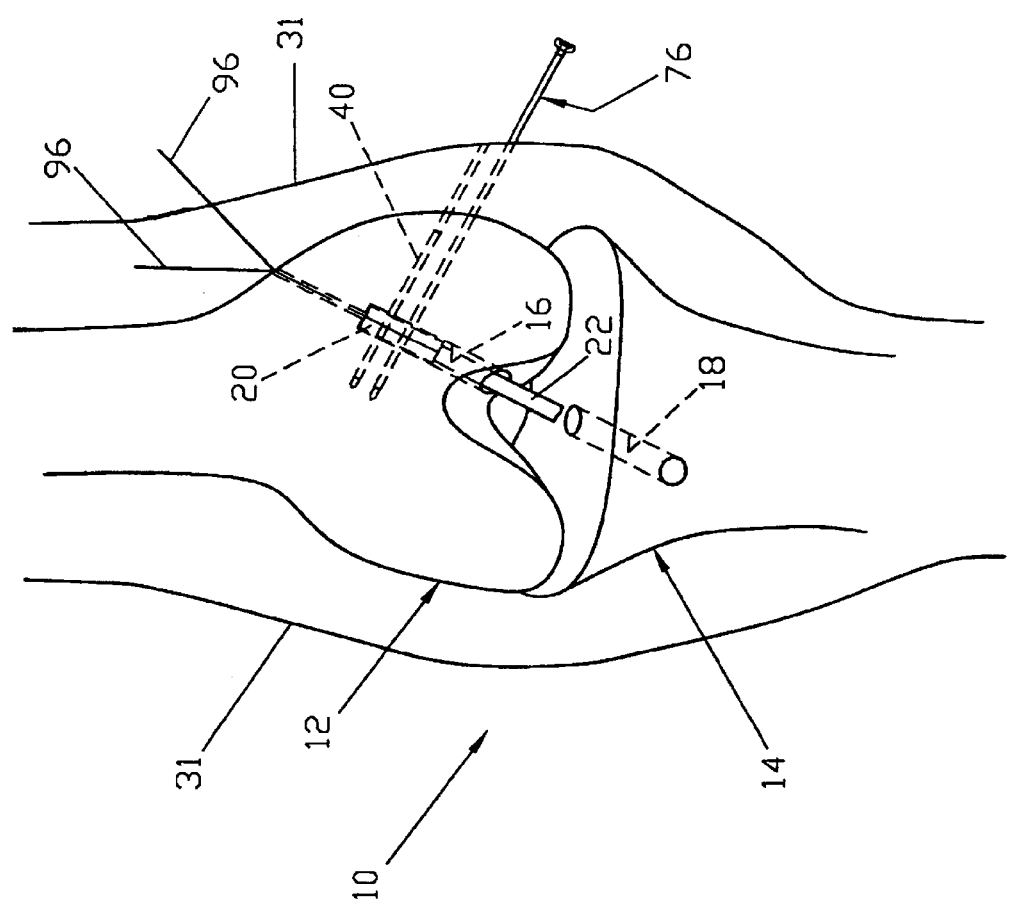

Trocar sleeve 76 and trocar 82 are then drilled through bone block 20, as shown in FIG. 24. Trocar 82 may then be removed from sleeve 76, placed in sleeve 74, and sleeve 74 and trocar 82 drilled through bone block 20, as shown in FIG. 25. The trocar 82 (or trocars 82 if more than one trocar is used) may then be withdrawn from the sleeve 74 (or sleeves 74, 76). The first absorbable rod 40 is then inserted, by sliding rod 40 through trocar sleeve 74 into a position extending through bone block 20 (FIG. 26). Sleeve 74 may then be withdrawn from bone block 20 and femur 12, leaving first absorbable rod 40 in place in femur 12 and extending through bone block 20, as shown in FIG. 27.

Figure 28:
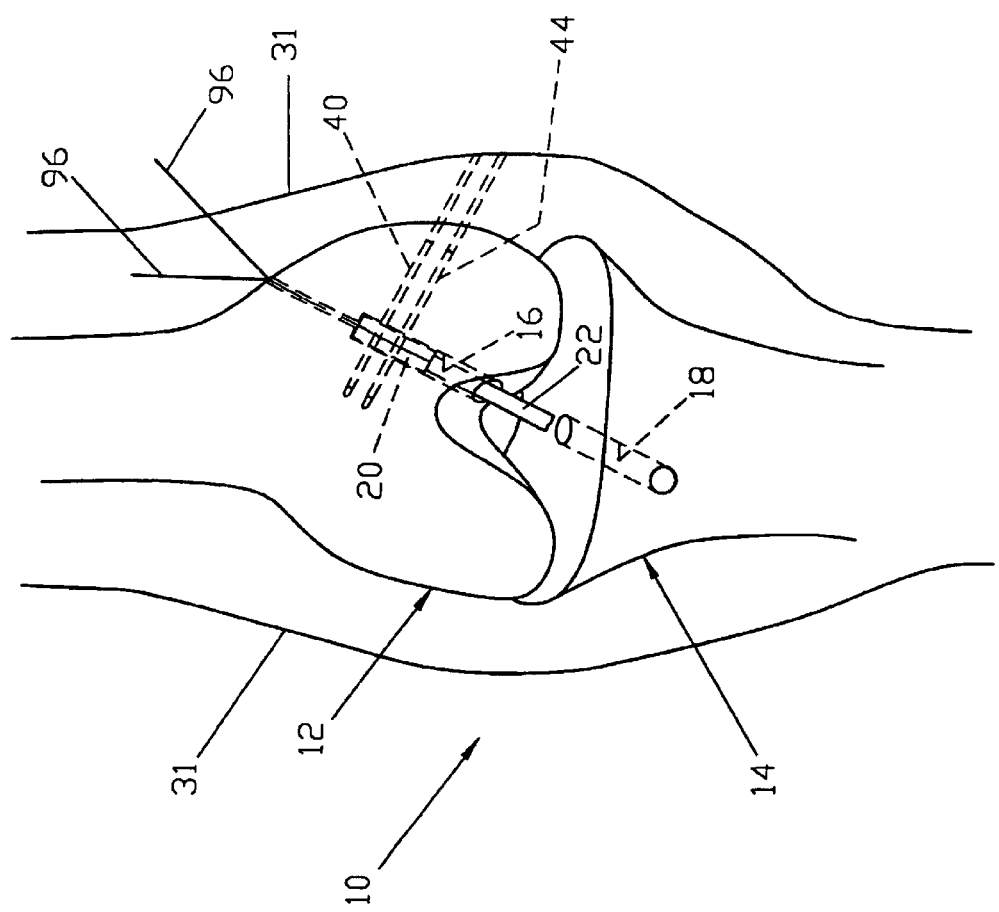
Figure 29:
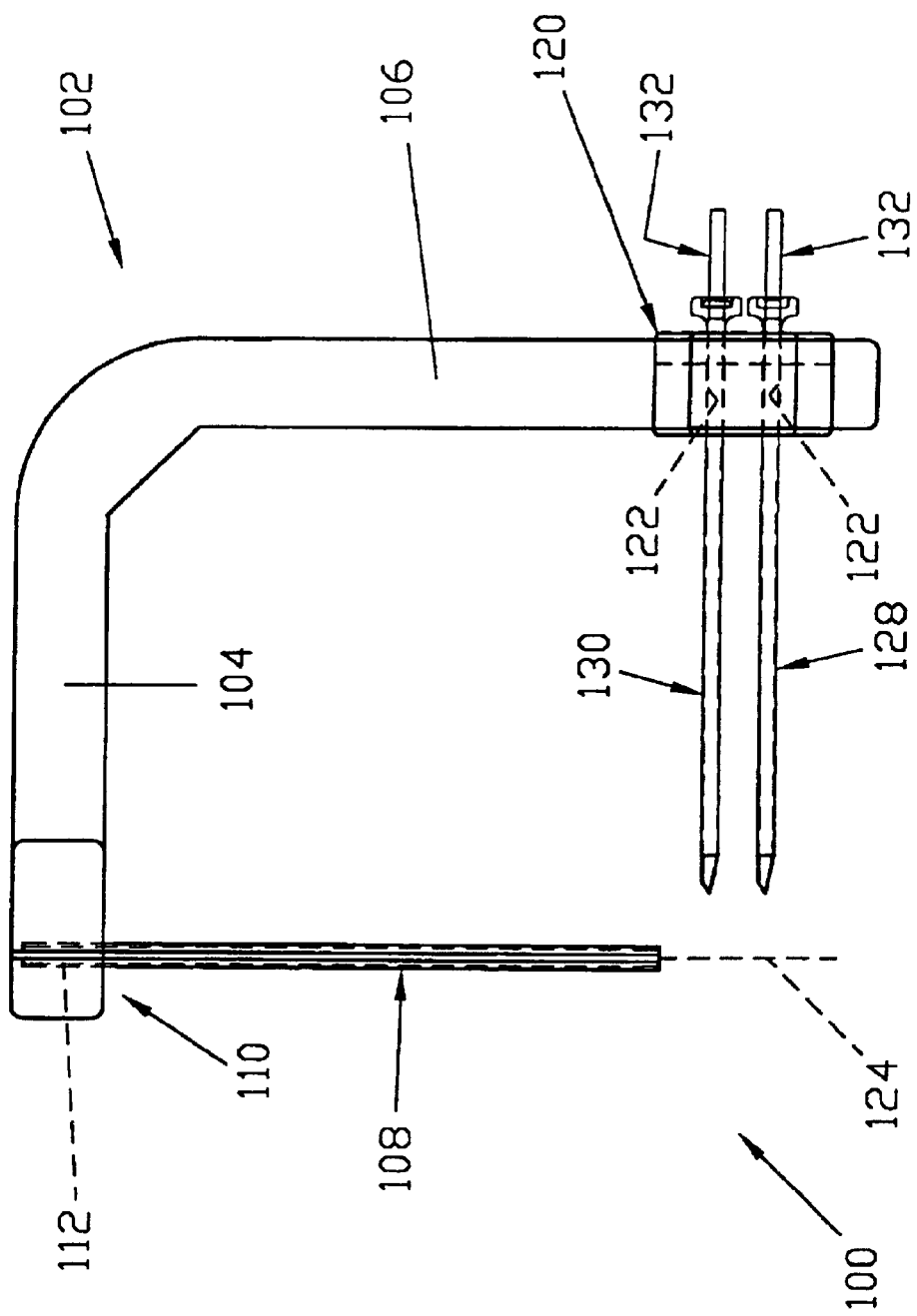
FIG. 29 is a side elevational view of another form of rack assembly for use in an alternative embodiment of the invention.
Figure 30:
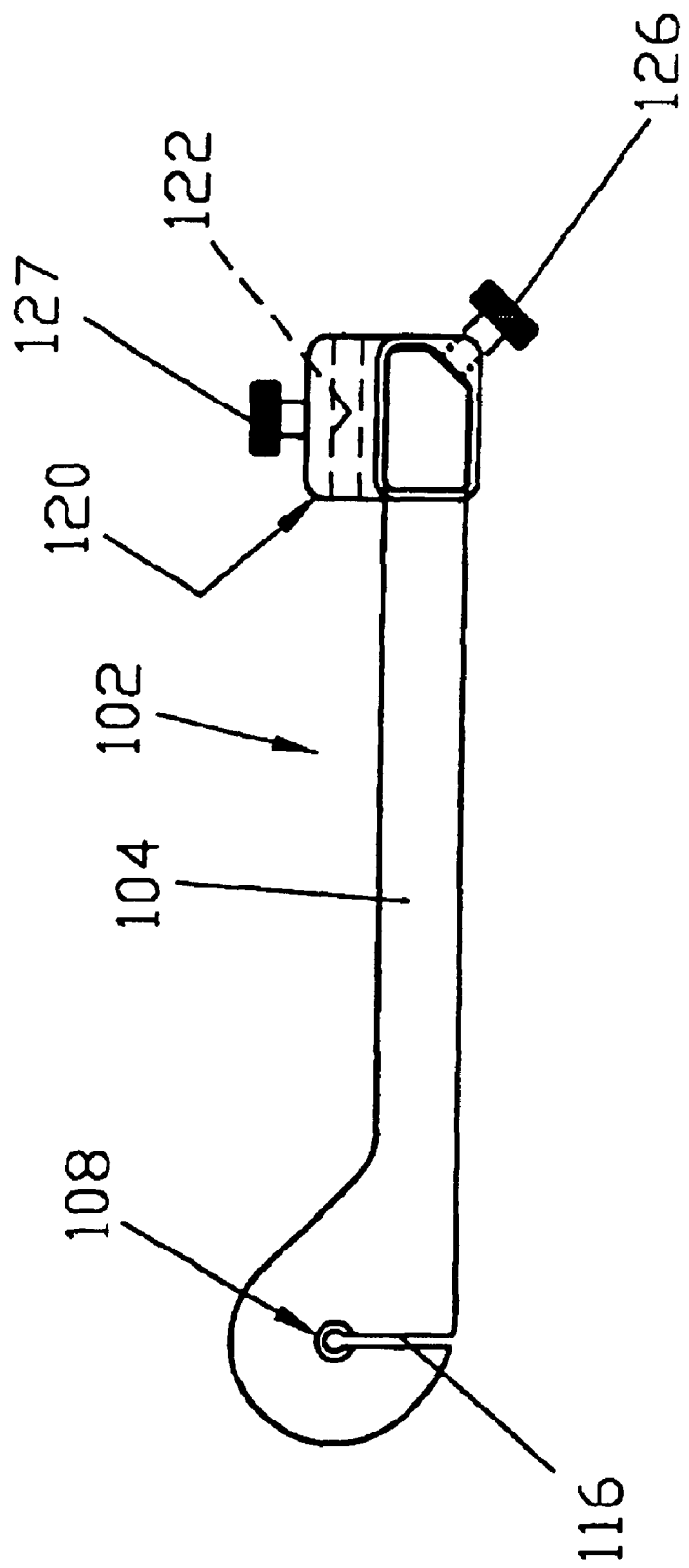
FIG. 30 is a bottom view of the rack assembly of FIG. 29.
Figure 32:
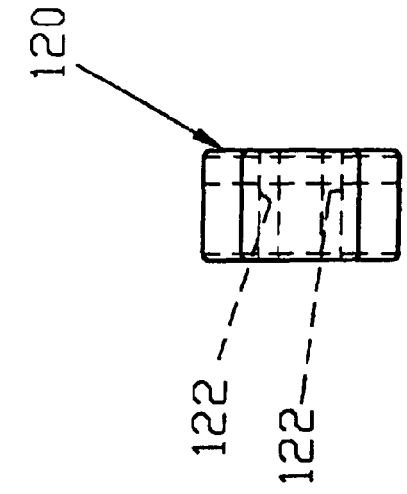
FIG. 32 is a side elevational view of the trocar sleeve guide member.
Figure 33:
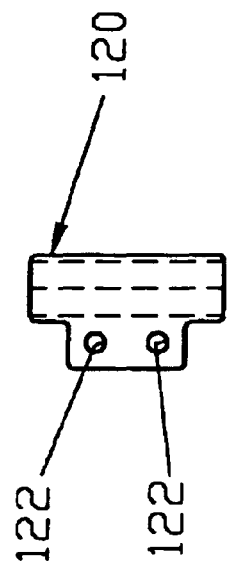
FIG. 33 is a front elevational view of the trocar sleeve guide member.
Figure 31:
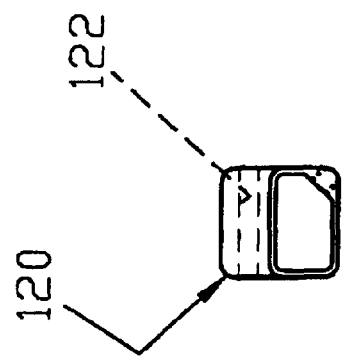
FIG. 31 is a bottom view of a trocar sleeve guide member portion of the rack assembly of FIG. 29.

Similarly, second absorbable rod 44 is then slid into place through sleeve 76. Sleeve 76 is then removed, leaving second absorbable rod 44, along with first absorbable rod 40, extending through bone block 20 so as to lock bone block 20 in place in femoral tunnel 16, as shown in FIG. 28.

It should be appreciated that it is also possible to provide rack assembly 50 with a guide member 70 which is not formed in two separable halves. In this situation, when the rack's L-shaped member 52 is to be withdrawn from the surgical site (see FIGS. 21 and 22), guide member 70 can simply be detached from L-shaped member 52 by unscrewing set screw 71. Guide member 70 can then be left mounted on the outboard portions of sleeves 74, 76 until sleeves 74, 76 are withdrawn from the surgical site, with guide member 70 being removed with the last of the sleeves 74, 76.

The present invention may also be practiced using the novel rack assembly 100 illustrated in FIGS. 29–33. Rack assembly 100 comprises an L-shaped member 102 having a base portion 104 and an arm portion 106. Arm portion 106 extends transversely of, and preferably is normal to, base portion 104.

Rack assembly 100 also includes a cannulated sleeve 108 which, at a base end 110 thereof, is connected to base portion 104. Cannulated sleeve 108 may be retained in a bore 112 in base portion 104, as by screw threads or a set screw (not shown) or a press fit or the like. Cannulated sleeve 108 is provided with a slot 114 (FIG. 29) extending substantially throughout the length of sleeve 108. Base portion 104 of L-shaped member 102 is also provided with a slot 116 (FIG. 30) which is alignable with the sleeve's slot 114 so as to place the slots 114, 116 in communication with each other.

A trocar sleeve guide member 120 is removably connectable to arm portion 106 of L-shaped member 102. Trocar sleeve guide member 120 is provided with bores 122 extending therethrough. Bores 122 extend substantially normal to a hypothetical extension of the longitudinal axis 124 of cannulated sleeve 108. A set screw 126 (FIG. 30) may be used to releasably retain trocar sleeve guide member 120 in position on arm portion 106. To assist in positioning trocar sleeve guide member 120 on arm portion 106 of L-shaped member 102, arm portion 106 may be provided with a stop means (not shown) for limiting movement of member 120 on arm portion 106. Trocar sleeve guide member 120 is preferably formed in two halves releasably held together by a set screw 127 (FIG. 30), whereby trocar sleeve guide member 120 can be slidably mounted on, or detachable from, trocar sleeves 128, 130 passing through bores 122, as will hereinafter be discussed.

First and second trocar sleeves 128, 130 are received by bores 122, such that sleeves 128, 130 are axially and rotatably movable in bores 122. The two trocar sleeves 128, 130 are substantially identical to the sleeve 74 shown in FIGS. 16 and 17. Rack assembly 100 also includes one or more trocars 132 for disposition in sleeves 128, 130. The trocar 132 is substantially identical to the trocar 82 shown in FIG. 15. The aforementioned first and second absorbable rods 40, 44 are slidable through sleeves 128, 130.

FIGS. 34–40 illustrate how rack assembly 100 may be used to practice the present invention.

Figure 34:
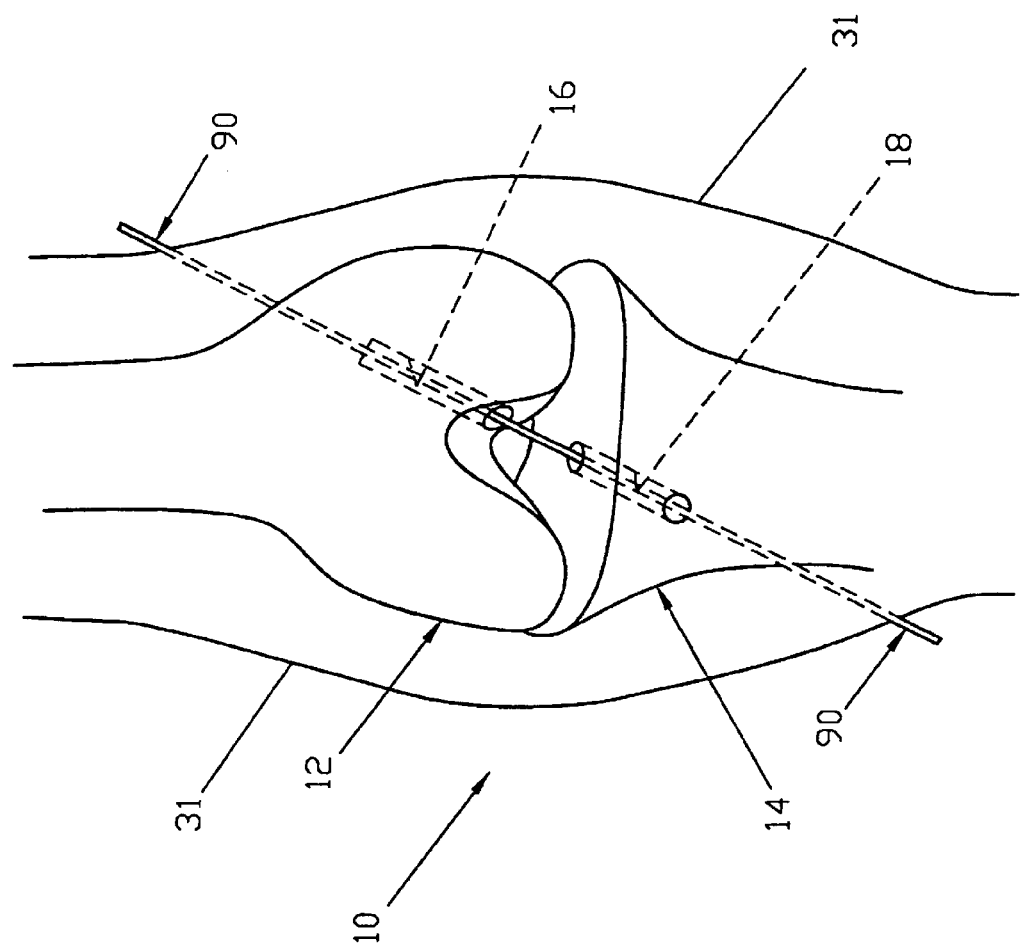
FIG. 34 is a view similar to that of FIG. 18.
Figure 35:
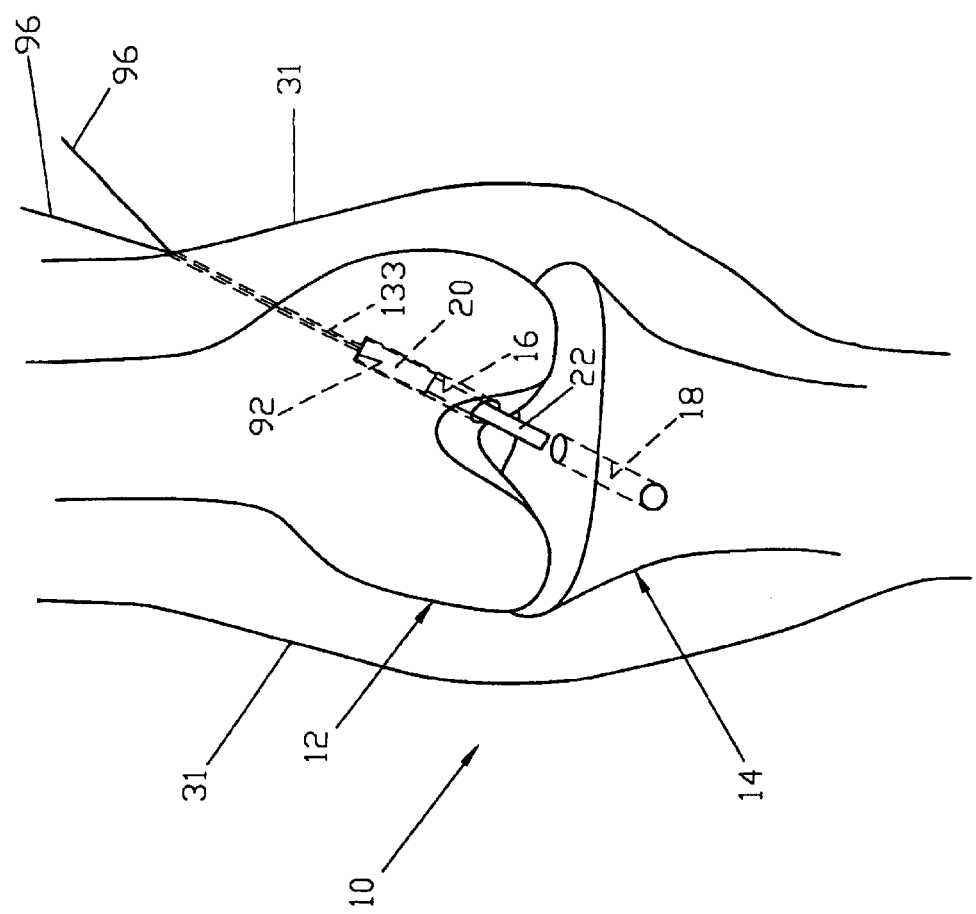
FIGS. 35–40 are diagrammatical views illustrating a series of steps in the use of the rack assembly of FIG. 29.

Referring now to FIG. 34, it will be seen that bone tunnels 16 and 18 are formed in femur 12 and tibia 18, respectively, and a guidewire 90 extends through bone tunnels 16, 18. Guidewire 90 is then used to pull a suture 96, which is attached to bone block 20, up through tibial tunnel 18 and into femoral tunnel 16, such that bone block 20 is in engagement with annular shoulder 92 (FIG. 35). Bone block 20 is kept in this position by maintaining tension on the portion of suture 96 emerging from the top of femur 12.

Figure 36:
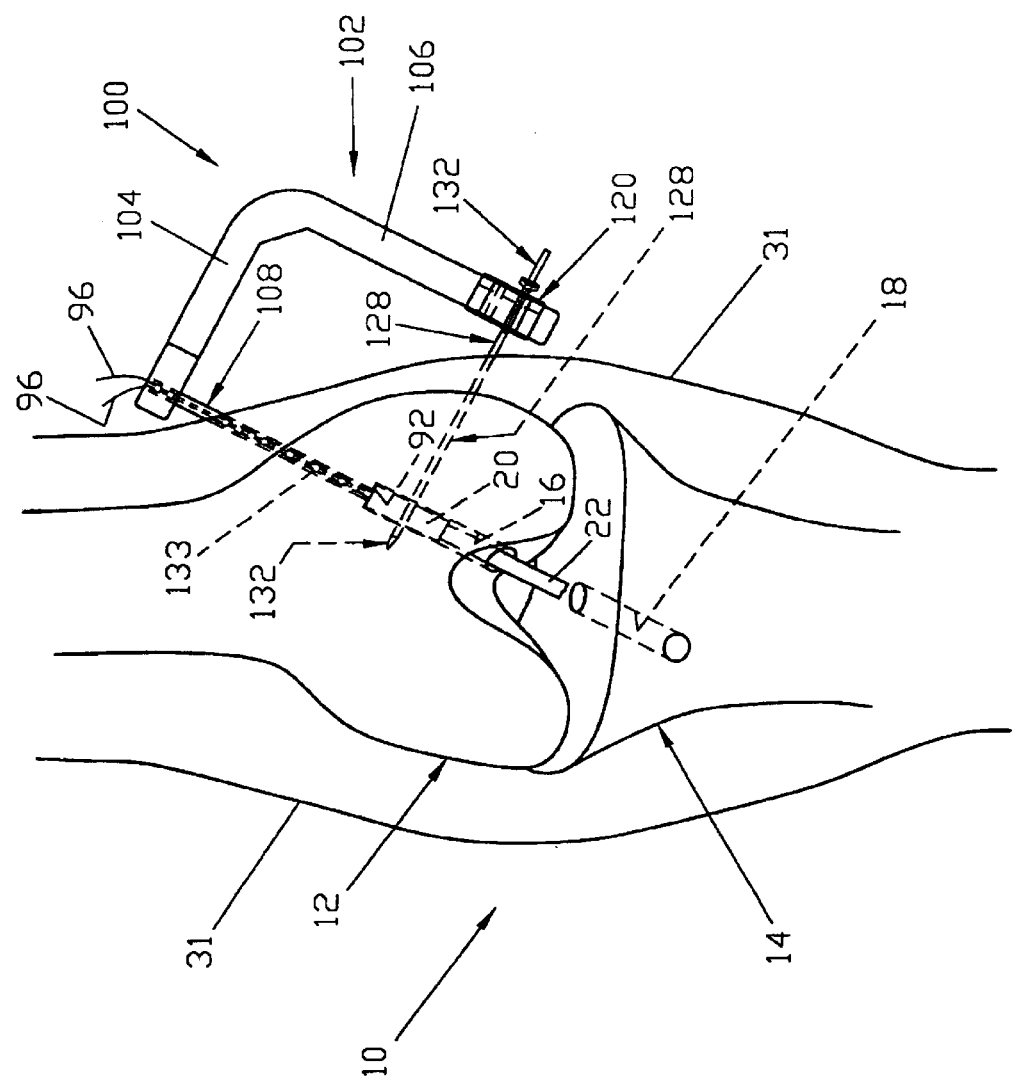
Figure 37:
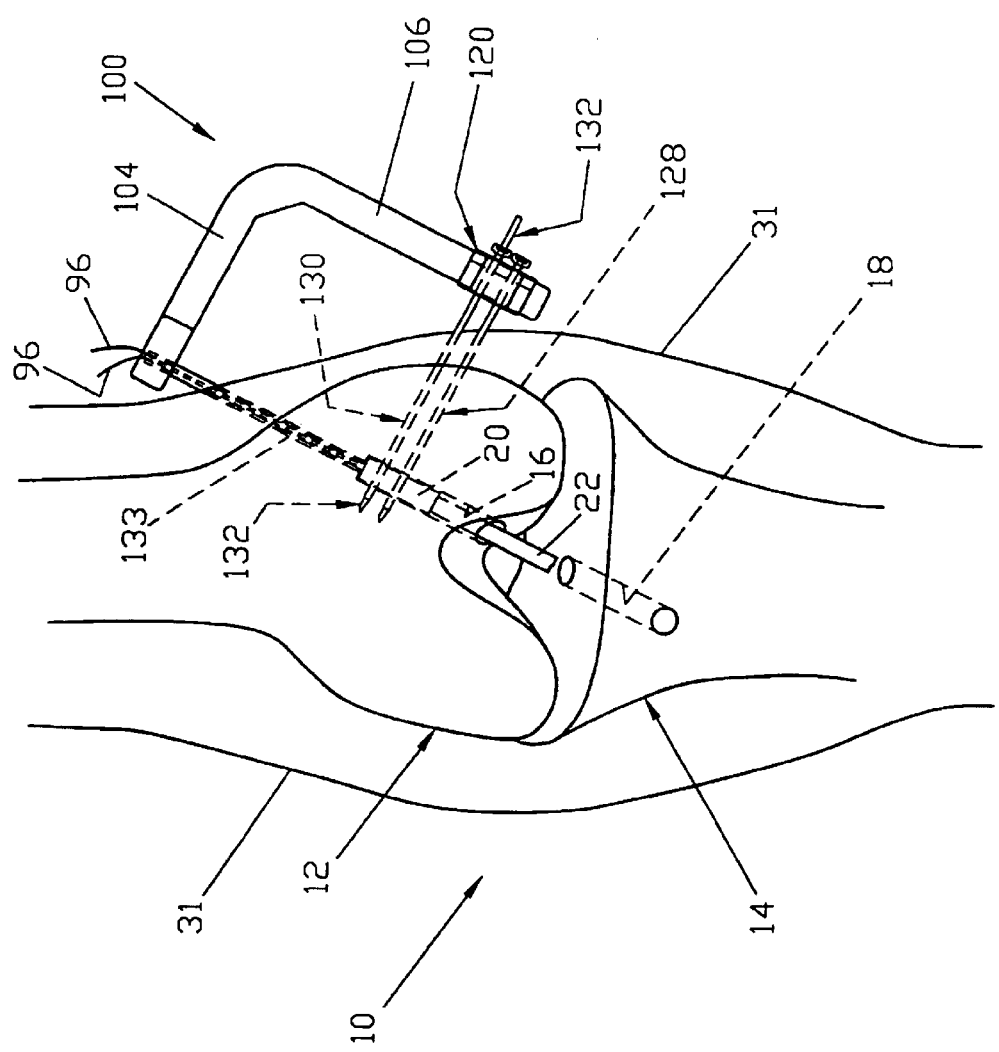

Suture 96 is then introduced into the rack assembly's cannulated sleeve 108 and base portion 104 by way of slots 114, 116. Cannulated sleeve 108 is then passed down the hole 133 (FIGS. 35 and 36) left by the removed guidewire 90 until the distal end of the cannulated sleeve engages the top end of bone block 20 (FIG. 36). Next, first trocar sleeve 128 is extended through a guide member bore 122 and a trocar 132 is inserted into sleeve 128. Alternatively, a trocar 132 may be inserted into first trocar sleeve 128 before first trocar sleeve 128 is inserted into a guide member bore 122. The sleeve 128 and trocar 132 are then drilled, as a unit, into femur 12. With bone block 20 held against shoulder 92 by pulling on suture 96, the combination of sleeve 128 and trocar 132 is drilled through bone block 20 (FIG. 36). In a similar manner, sleeve 130 and trocar 132 (either the same trocar used with sleeve 128 or another trocar) are then drilled through bone block 20, as shown in FIG. 37.

Figure 38:
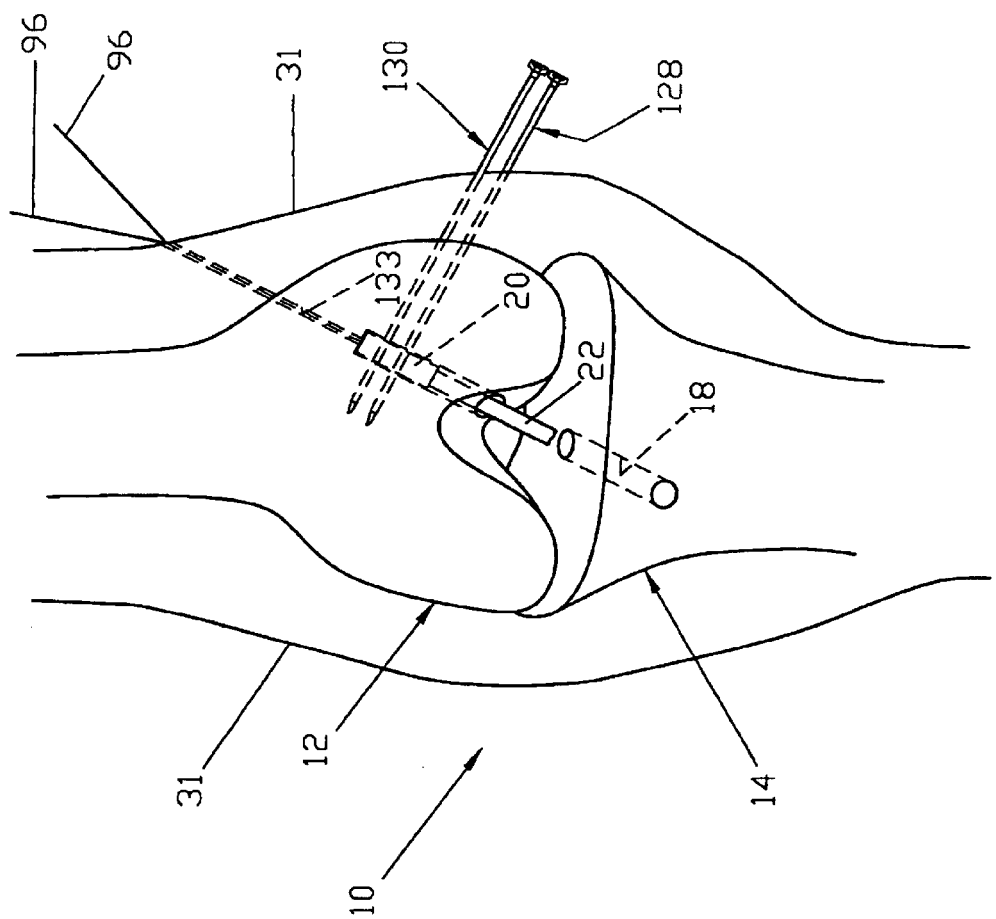
Figure 39:
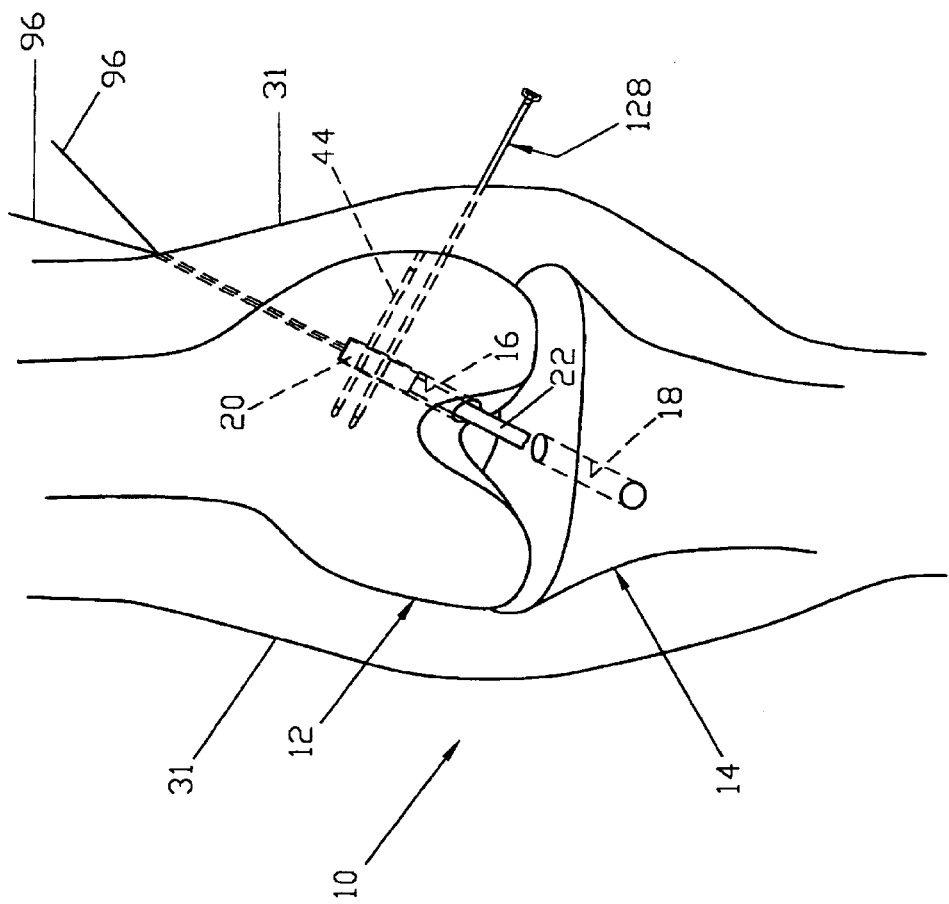
Figure 40:
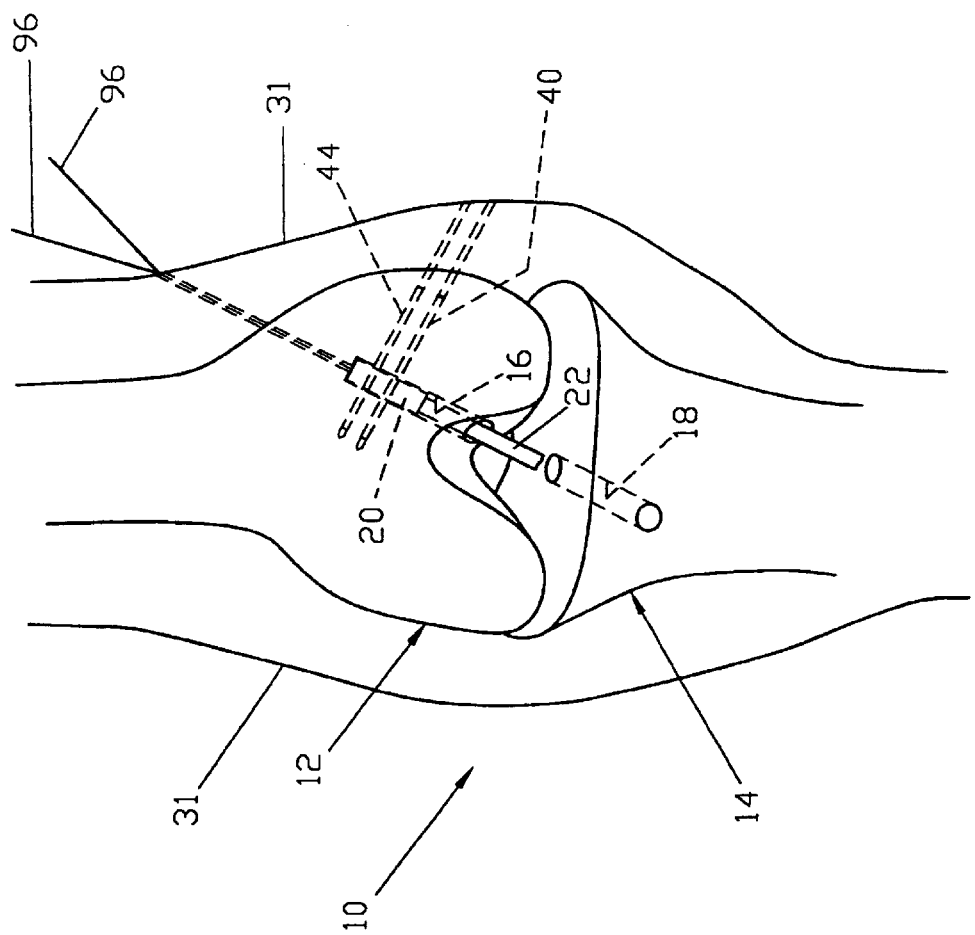
Figure 51:
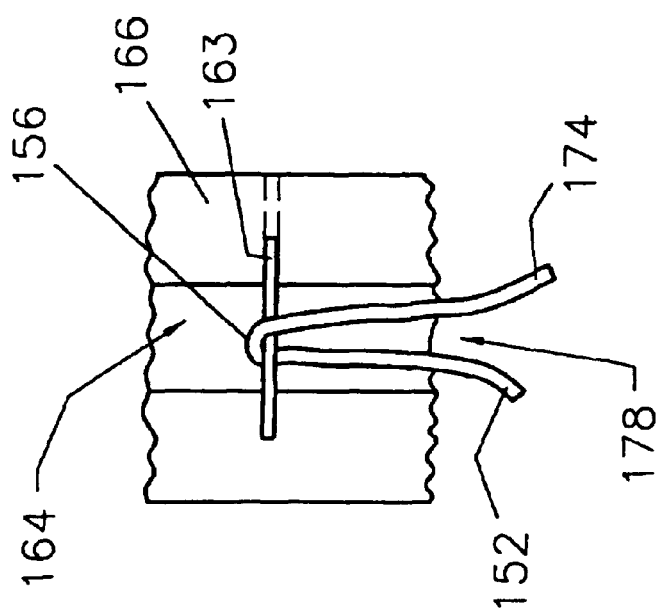

L-shaped member 102 and cannulated sleeve 108 are then removed from the surgical site. This may be accomplished by first loosening set screw 127 (FIG. 30) so as to separate trocar sleeve guide member 120 into its two halves, whereby trocar sleeves 128, 130 will be freed from guide member 120, and then sliding cannulated sleeve 108 upward and out of hole 133. Any trocars 132 are then removed, leaving the trocar sleeves 128, 130 extending into femur 12 and across bone block 20, as shown in FIG. 38.

Second absorbable rod 44 is then slid through sleeve 130 and sleeve 130 removed (FIG. 39), and first absorbable rod 40 is slid through sleeve 128 and sleeve 128 removed, leaving absorbable rods 40, 44 in place (FIG. 40) holding bone block 20 locked in femoral tunnel 16.

Suture 96 is then slipped through bone block 20 and removed, in the manner well known in the art.

It is to be understood that the present invention is by no means limited to the application thereof as herein disclosed and/or as shown in the drawings. For example, for illustrative purposes, the inventive method is described herein and illustrated with reference to the human knee joint. It is foreseen that the method described herein will be particularly beneficial with respect to such operations. However, it will also be appreciated by those skilled in the art that the method described herein may find utility with respect to mammals generally, and with respect to other bones as, for example, in shoulder joints or the like.

By way of further example, trocars 82 and 132 and their associated sleeves 74, 76 and 128, 130, respectively, might be passed only part way through bone block 20, but not all the way through; or sleeves 74, 76 and/or sleeves 128, 130 might be stopped short of bone block 20 while trocars 82 and/or 132 penetrate into bone block 20.

Furthermore, trocars 82 and 132 are disclosed herein as being in the form of a hard rod with a sharp tip for penetrating bone. Thus, for example, trocars 82 and 132 might comprise guidewires or K-wires with a pyramidal front point. Alternatively, however, the invention might also be practiced with trocars 82 and 132 comprising a twist drill, a spade drill and/or some other sort of drill.

Also it is contemplated that trocars 82 and/or 132 might be used with their associated rack assemblies 50 and 100, respectively, but without their associated sleeves 74, 76 and 128, 130, respectively. In this case, at least one trocar would always remain positioned in bone block 20 until at least one absorbable rod 40, 44 was positioned in the bone block.

If desired, it is also possible to practice the present invention using just one sleeve 74 and one trocar 82, or just one sleeve 76 and one trocar 82; and it is possible to practice the invention using just one sleeve 128 and one trocar 132, or just one sleeve 130 and one trocar 132. In such a situation, the sleeve element would serve to retain the bone block in position within the bone tunnel while the trocar is replaced by the rod which will ultimately hold the bone block to the bone.

It should also be appreciated that the present application will have utility with respect to setting cross-pins which may not necessarily be absorbable. In particular, the present invention will have utility wherever cross-pinning needs to be achieved for cross-pins which cannot be passed directly through the bone and/or bone block, e.g., where the cross-pins may be too soft or too brittle or too fragile to pass directly through the bone and/or bone block, or where the cross-pins may have a geometry which makes it difficult or impossible for them to be passed directly through the bone and/or bone block. By way of example, the present invention might be used to set cross-pins made out of plastic and/or ceramic materials, or the present invention might be used to set cross-pins made out of metal.

In addition, numerous other alternatives are contemplated within the scope of the present invention in its broadest aspects.

More particularly, it will be understood by those skilled in the art that there are many instances wherein it is desired to locate a portion of a piece of soft tissue, such as a ligament, tendon or the like, within a bone tunnel, without a bone block attached to it. This may occur, for example, where a prosthetic substitute for a ligament, tendon or the like is to be used to effect a repair, or in those instances wherein it is undesirable for one reason or another to harvest a repair graft from elsewhere in the patient's body along with a bone block naturally attached to one end of the graft.

In such cases, a portion of the piece of tissue alone may be cross-pinned in a bone tunnel by any of the methods discussed above. Specifically, as shown in FIGS. 41 and 42, the portion 150 of the piece of tissue 152 to be cross-pinned in the bone tunnel is preferably folded back upon itself one or more times. When this is done, tacking stitches 154 may be used to hold the layers 156 of folded tissue together while the resulting mass 150 is inserted or pulled into the bone tunnel in a manner similar to the procedures used to locate a bone block in a bone tunnel discussed above. Thereafter, cross-pinning proceeds substantially as discussed above, such that the rods 158 ultimately extend either through the tissue mass (see phantom lines in FIG. 41), or between the folded tissue layers (see phantom lines in FIG. 42), or both.

In this alternative, the chances of the rod and/or sleeve and/or trocar tearing laterally out of, or longitudinally along, the tissue 152 may be significant. This is particularly the case in those instances wherein the repair is to be subjected to substantial stress prior to complete healing. Accordingly, it is often desirable to reinforce the portion 150 of the tissue 152 to be cross-pinned within the bone tunnel. This may be accomplished in numerous ways well known to those skilled in the art. One such alternative, representatively shown in FIG. 43, is to "whip stitch" the portion 150 of the tissue 152 which is to be cross-pinned within the bone tunnel. This creates a braid-enclosed, substantially solid mass 160 adapted to receive the rods 158, and adds the strength of the numerous passes of the cord-like material 162, extending through the tissue as used to form the "whip stitch", to alleviate the tear-out problem referred to above. In addition, "whip stitching" is well understood by surgeons, and relatively easy to do. Therefore, this alternative avoids certain complications which may arise during the harvesting of tissue grafts with bone blocks attached; avoids trimming bone blocks to fit bone tunnels during surgical procedures; and provides a simple, fast and efficient way to cross-pin the tissue in a bone tunnel, with minimal added trauma to the patient.

As noted above, the foregoing procedures may also be used to secure artificial grafts in the bone tunnel, i.e., grafts comprising an artificial prosthetic device not harvested from the body. In such a case, it may or may not be desirable to fold the graft back upon itself one or more times, in the manner shown in FIGS. 41–43, prior to cross-pinning.

Similarly, a portion 150 of a piece of tissue 152 may be fixed in a bone tunnel by positioning a bio-absorbable rod 163 diametrically across the bone tunnel 164, and thereafter pulling the portion 150 of the piece of tissue 152 into an open end of the bone tunnel, around the rod 163 and back out the same open end of the bone tunnel. More particularly, as best seen in FIGS. 44–51, it has been found that the positioning of a bio-absorbable rod 163 diametrically across bone tunnel 164 is best accomplished with a trocar/sleeve combination 171 such as that illustratively shown in FIGS. 15–17. This is because in any alternative wherein a means such as a sharpened k-wire, trocar or the like is used without an accompanying sleeve to form an opening through the bone 166, through the bone tunnel 164, and into the bone 166 on the opposite side of the bone tunnel 164, it is difficult to remove the hole-forming device and to replace it with a rod 163. Typically, the rod 163 will pass through the opening 168 (FIG. 49) and through the bone tunnel 164 easily, however, it is often not as easy to locate and engage opening 170 on the other side of bone tunnel 164 with the forward end of rod 163.

Accordingly, in the practice of this alternative, it is preferred that a trocar/sleeve combination 171 be drilled in the manner discussed in detail above into bone 166, transversely to the longitudinal axis 172 (FIG. 44) of bone tunnel 164, diametrically through bone tunnel 164, and into bone 166 on the opposite side of bone tunnel 164 (see FIGS. 44 and 45). Thereafter, the trocar 171a is removed from sleeve 171b, and a bio-absorbable rod 163 is inserted into sleeve 171a so as to occupy a position extending across bone tunnel 164 (see FIGS. 46–48). Sleeve 171b is then removed from bone 166 and rod 163, leaving rod 163 extending from opening 168, diametrically across bone tunnel 164 and into opening 170 (see FIG. 49).

Figure 50:
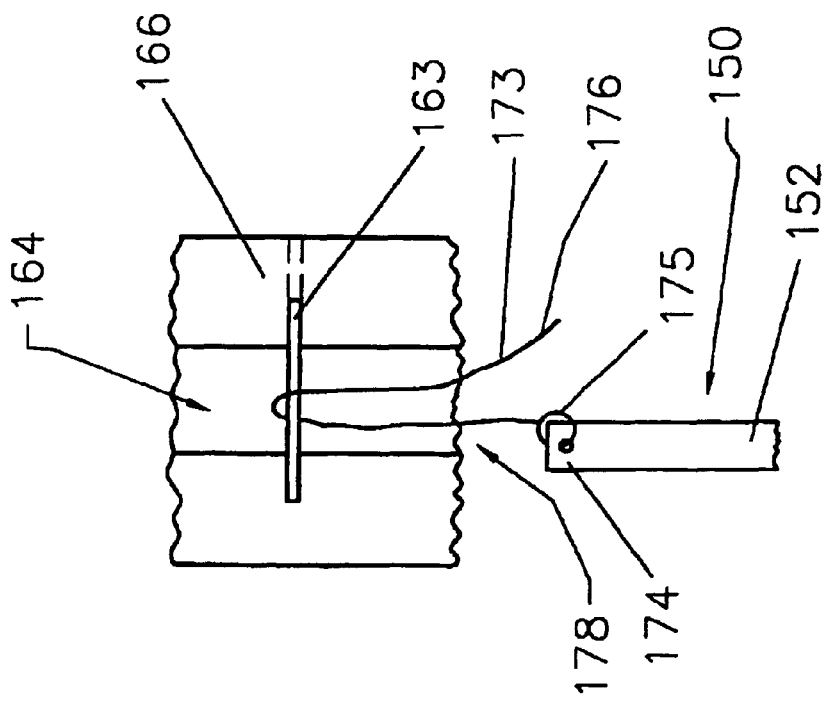

At this point in the procedure, or earlier if desired, one end 175 of a length of cord-like material, such as suture 173, is secured to an end 174 of piece of tissue 152 (FIG. 50). The other end 176 of the length of cord-like material 173 is then threaded into an open end 178 of bone tunnel 164, and thence around rod 163, and then back out open end 178 of bone tunnel 164 (see FIG. 50). Finally, the free end 176 of the cord-like material 173 is pulled so as to draw portion 150 of piece of tissue 152 into open end 178 of bone tunnel 164, around bio-absorbable rod 163, and back out open end 178 of bone tunnel 164. Tissue portion 150 thus assumes a generally U-shape, having its closed end slidably secured in bone tunnel 164 by bio-absorbable rod 163, and its free ends extending outwardly from the same open end 178 of bone tunnel 164 (see FIG. 51).

As noted above, the foregoing procedure may also be used to secure artificial grafts in the bone tunnel, i.e., grafts comprising an artificial prosthetic device not harvested from the body.

Figure 53:
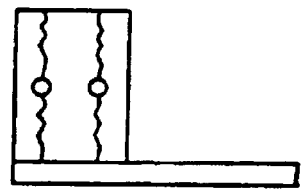
FIGS. 52 and 53 are illustrative side elevational views of representative bone blocks showing two possible examples of how a bone block may fracture during or after the placement of a cross-pin therethrough.
Figure 52:
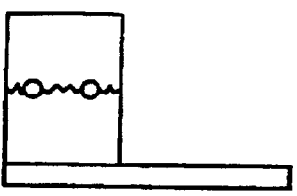

Still further, it has been found that, in practice, bone blocks are relatively hard. This is frequently the case where the bone block is formed out of cortical bone. In addition, it can also sometimes be relatively difficult to drill a trocar/sleeve combination through bone 166, particularly where bone 166 comprises a substantial layer of cortical bone. Consequently, it can be difficult to drill a trocar/sleeve combination (see, for example, FIG. 55) through the bone, and into and/or through the bone block. In addition, even if this drilling is successfully accomplished, the bone block may fracture, as shown, for example, in FIGS. 52 and 53. In this respect it is noted that the possibility of bone block fracture may be reduced by reducing the diameter of the trocar/sleeve combination, and hence the resulting hole through the bone block, but this may in turn lead to an increase in the possibility of rod breakage when a load is applied to the graft ligament.

Two alternatives have been developed to address these problems.

Figure 54:
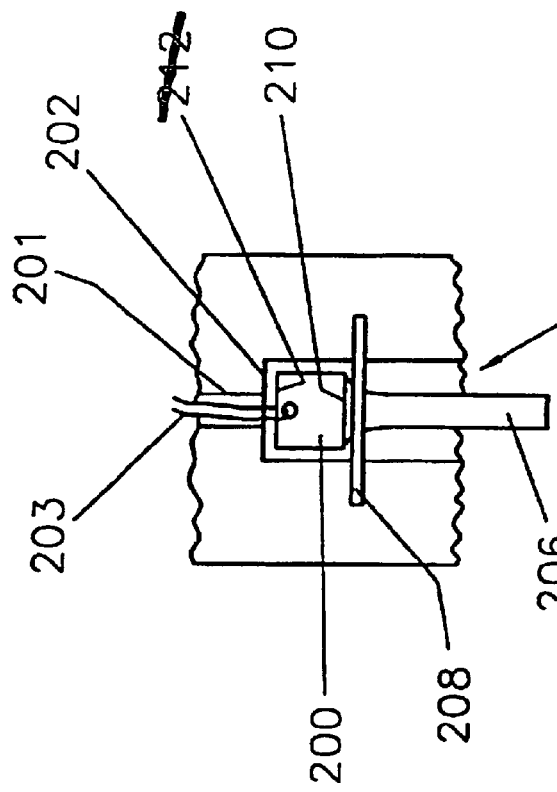
FIG. 54 is an illustrative sectional side elevational view of a bone block located in a partially closed ended bone tunnel and fixed in position by a rod extending across the bone tunnel between the bone block and the open end of the bone tunnel.

In the first of these alternatives, best seen in FIG. 54, the solution utilizes the facts that (1) a bone block is significantly stronger in compression than it is in tension, and (2) a larger diameter rod will provide a stronger bone block fixation in a bone tunnel if bone block fracture is not an issue. Specifically, the bone block 200 is located at substantially closed end 202 of substantially blind bone tunnel 204, with its associated tissue graft 206 extending outwardly from the open end 208 of the substantially blind bone tunnel 204. It will be understood that a guide hole 201 may extend through substantially closed end 202 of bone tunnel 204 so as to allow bone block 200 to be drawn into bone tunnel 204 by a cord-like element 203, or otherwise located in bone tunnel 204 as discussed hereinabove. A rod 208, as much as 30% larger in diameter than a rod suitable for emplacement through bone block 200, is then located diametrically across bone tunnel 204 adjacent to proximal end 210 of bone block 200. In this case, rod 208 is positioned utilizing the same method as described above with regard to the threading of a portion of a piece of tissue over a rod extending diametrically through a bone tunnel (see FIGS. 44–51). Also, the rod 208 may pass through the tissue graft 206, or not, as desired. The result is that bone block 200 is reliably fixed in bone tunnel 204 between substantially closed tunnel end 202 and rod 208.

The second of the above-mentioned alternatives proceeds from the premise that if the sleeve does not have to extend into or through the bone block, a significantly larger diameter rod may be used with a corresponding increase in the strength of the fixation of the bone block in the bone tunnel. This alternative is representatively shown in FIGS. 56–63, which will be referred to specifically below.

In this case, the trocar/sleeve combinations 210 (see FIG. 55) are drilled through the skin and into the bone in the same manner as discussed in detail above, and the bone block is located in the bone tunnel such that the various elements reside in a configuration generally as depicted in FIG. 22. At this point, the trocars are disengaged from the sleeves, the bone block is pulled up into the bone tunnel (FIG. 23), and rods are inserted through (i) the sleeves and (ii) the bone located between the distal ends of the sleeves and the bone tunnel, and then into the bone block.

Figure 60:
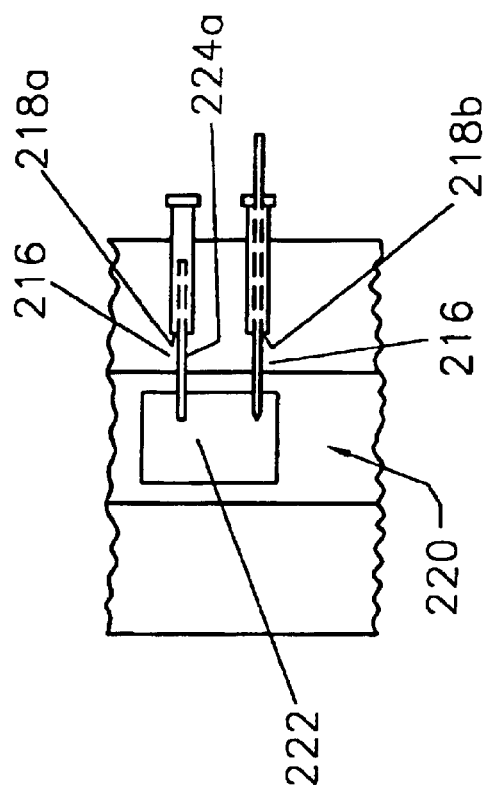
Figure 61:
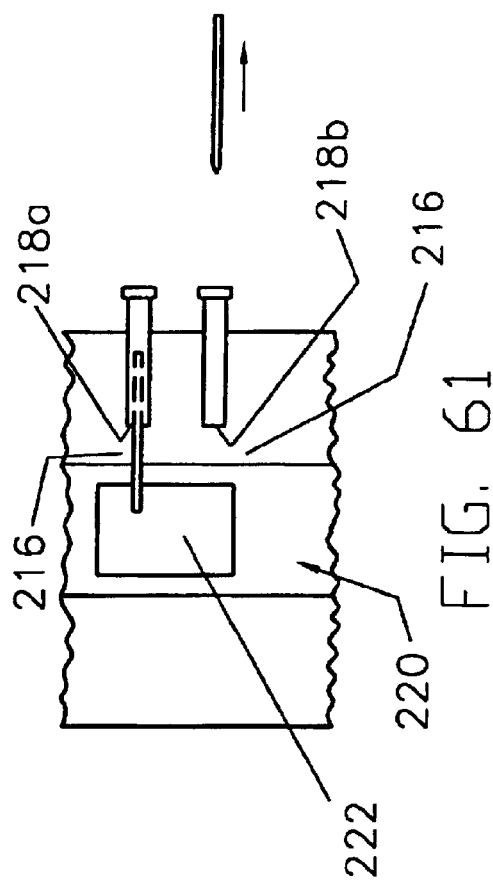

The latter insertion step may be accomplished in any one of several different ways. For example, a second, longer trocar 212a, 212b may be inserted into each of the sleeves 214a, 214b and either drilled (FIG. 57) or tapped (FIG. 58) through the bone 216 located between the distal ends 218a, 218b of the sleeves 214a, 214b, and then into the bone tunnel 220 and into the bone block 222. Thereafter, one of the longer trocars 212 is removed (FIG. 59), and a metal, plastic, ceramic or bio-absorbable rod 224a is inserted into the bone and the bone block through the sleeve (FIG. 60). This is followed by the removal of the other longer trocar 212 (FIG. 61) and the insertion of another rod 224b into the bone and bone block through the second sleeve (FIG. 62). Finally, the sleeves are removed from the patient (FIG. 63).

In the last discussed alternative, the longer trocars 212a and 212b are commonly stepped, e.g., in the manner shown in FIG. 24. More particularly, the longer trocars 212a commonly include a distal portion 230 having a smaller transverse cross-sectional diameter than their proximal portion 232, and define a distally-facing radial shoulder 234 at the joiner of their proximal and distal portions. In this way, the extent of trocar penetration beyond the distal ends of the sleeves is controlled by pre-selecting the axial length of the distal portion of the longer trocars. More specifically, the longer trocars are allowed to penetrate beyond the distal ends of the sleeves only to the point at which their distally-facing radial shoulders engage either the bone at the distal ends of the sleeves, or a radially-disposed, inward projection 236 formed on the sleeve side wall (FIG. 65).

Alternatively, rigid rods 224a, 224b may be driven through the sleeves 214a, 214b, through the bone 216 located between the sleeves and the bone tunnel 220, and then into the bone block 222 directly. This may be accomplished by, preferably, pointing or rounding the distal ends of the rods 224a, 224b, inserting the rods into the sleeves 214a, 214b, and using a plunger shaft 238 and tapping means 240 to drive the rods into position through the bone and into the bone block (FIG. 66).

It further has been found, that in the interlocking trocar/sleeve assembly shown in FIGS. 15–17 and 55, the radial shoulder 242 (FIG. 55), formed by the distal end of the sleeve 248 proximally of the pointed distal end 244 of the trocar extending distally thereof, can be a significant impediment to the passage of the interlocked trocar/sleeve combination into bone. Indeed, in practice, this shoulder, while normally only about 0.005 to 0.010 inch in radial thickness, has been noted to cause burning of the bone as the trocar/sleeve combination is advanced through the bone toward the bone tunnel. To correct this problem, the distal edge 242 of the sleeve could be bevelled at an angle substantially equal to that of the adjacent trocar point 244 (see FIG. 67). This is not preferred, however, in view of the variations in machining tolerance commonly acceptable in the art in the formation of bevelled edges and trocar points. In particular, the chance of an exact mating of the trocar point with a bevelled sleeve end is unlikely. Hence, the bone burning problem, and more generally the problem of the resistance to penetration of the trocar/sleeve combination into the bone, are still present in the embodiment shown in FIG. 67, albeit to a perhaps smaller degree than in the FIG. 55 embodiment.

To solve this basic problem, it has been found that the distal end 246 of the sleeve 248 should be slanted at an angle of approximately 15° proximally relative to a plane 250 located normal to the longitudinal axis 252 of the sleeve (see FIG. 68). In the resulting construction of the trocar/sleeve assembly, the trocar point 256 drills into the bone in the same manner as previously described, while the slanted distal end 246 of the sleeve 248 cuts into the sidewall of the hole formed by the trocar point, instead of rotating flat against the bone surrounding the hole being formed by the trocar. As a practical matter, this alternative is deemed to be of significant importance, inasmuch as the ease of use of the methods and apparatus described herein affects their commercial utility. A bone drill which does not exhibit a tendency to bind, and/or to burn the bone during use, is significantly more desirable than a bone drill which does bind or burn the bone during use.

Accordingly it will be understood that, currently, one preferred method of practicing the present invention includes the following steps:

(1) drilling at least two trocar/sleeve assemblies, of the type depicted in FIG. 68, into the bone to a position similar to that shown in FIG. 22 (note: this may be accomplished by sequentially and separately mating a single trocar with each sleeve and drilling that assembly into the bone);

(2) removing the trocar(s) from the sleeves so as to leave the sleeves extending through the skin and into the bone, but not intersecting the bone tunnel;

(3) removing the rack assembly (see element 52 in FIG. 21) from the sleeves and the bone tunnel;

(4) locating a bone block in the bone tunnel in alignment with axial projections of the sleeves;

(5) using a first, elongated, stepped trocar (see FIG. 64) to drill through the bone between the distal end of the first sleeve and the bone tunnel, through the bone block, and a pre-selected distance into the bone on the opposite side of the bone tunnel;

(6) with the first, elongated stepped trocar extending through the bone and the bone block, using a second, elongated stepped trocar to drill through the bone between the distal end of the second sleeve and the bone tunnel, through the bone block, and a pre-selected distance into the bone on the opposite side of the bone tunnel;

(7) removing the second trocar from the bone, the bone block and the second sleeve;

(8) inserting a rigid rod (of bio-absorbable, or non-bio-absorbable, material) through the second sleeve to a position wherein it extends through the bone block and engages openings on opposite sides of the bone tunnel as formed by the second elongated stepped trocar;

(9) removing the first trocar from the bone, the bone block and the first sleeve;

(10) inserting another rigid rod (of bio-absorbable, or non-bio-absorbable, material) through the first sleeve to a position wherein it extends through the bone block and engages the openings on opposite sides of the bone tunnel as formed by the first elongated stepped trocar; and

(11) removing the first and second sleeves from the patient.

The last mentioned alternatives also provide advantageous settings for the use of certain modifications to the above-described cross-pinning apparatus. For example, in the embodiment of the rack assembly discussed above wherein the cannulated sleeve 58 has an enlarged head 62 adapted for location in a bone tunnel transversely of the trocar/sleeve assemblies which are being drilled into the surrounding bone (FIGS. 19–21), a flattened head 258 (FIG. 69) defining a window 260 therethrough might be used in place of the enlarged head 62. In such a case, the flattened head 258 would extend substantially diametrically across the bone tunnel 262 in a plane transverse to an axial projection of the trocar/sleeve assemblies 264 being drilled into the bone. Further, the window 260 would be so disposed that the trocar/sleeve assemblies (or the trocars alone) could penetrate into the bone tunnel, through the window 260 in the head of the cannulated sleeve 266, and then into the bone on the opposite side of the bone tunnel.

More particularly, as shown in FIG. 69, this embodiment of the present invention is useful in any situation in which it is desired to form diametrically opposed openings in the sidewall of a bone tunnel. Particular examples of such situations include those wherein the length of the sleeve and the length, and rigidity, of the rods are such that they may be relied upon to ensure that a rod entering the bone tunnel from the drill means entry side thereof will be maintained in alignment with, and engage, the opening on the other side of the bone tunnel. Thus, those cases mentioned above wherein a rigid rod is passed through an object in a bone tunnel may find this alternative beneficial.

Finally, it is to be understood that the interlocking trocar/sleeve assemblies discussed hereinabove have numerous other uses beyond the cross-pinning of objects in bone tunnels. One such illustrative use is in the placement of absorbable, or non-absorbable, pins across bone fractures so as to assist in maintaining broken bones in a desired healing relationship after fracture reduction procedures have been completed. As depicted in FIGS. 70–74, this method follows the now well-understood steps of drilling a trocar/sleeve assembly into the desired position in bone, removing the trocar, inserting a rod into the sleeve, and then removing the sleeve from the bone and the rod.

Other illustrative uses of the devices and concepts of the present invention may include, among others, the removal of tissue from the interior of bones, and/or the delivery of other things into the interior of a bone, such as other devices or prostheses, drugs, bone graft material, substitute bone marrow, and so on.

Numerous further variations, alterations, modifications and other derivations of the present invention will occur and/or become obvious to those skilled in the art in view of the foregoing detailed description of the preferred embodiments of the present invention. Accordingly, it is to be understood that the foregoing specification and the appended drawings are intended to be illustrative only, and not as limiting of the invention.

What is claimed is:

1. A method for fixing a piece of tissue in a bone tunnel in a bone, the method comprising the steps of:
    advancing a first trocar and sleeve assembly through the bone and toward the bone tunnel;
    advancing a second trocar and sleeve assembly through the bone and toward the bone tunnel;
    each of the assemblies comprising a trocar disposed within a sleeve and having a sharpened end extending beyond an end of the sleeve, the trocar substantially filling the sleeve within which the trocar is disposed;
    the first and second assemblies being advanced spaced apart and generally normal to the bone tunnel;
    placing a bone block having the piece of tissue attached thereto in the bone tunnel;
    withdrawing the first trocar from the first sleeve, leaving the first sleeve in the bone;
    advancing a first bio-absorbable rod into the first sleeve and through the bone block;
    withdrawing the first sleeve from the bone block and the bone, leaving the first bio-absorbable rod in place;
    withdrawing the second trocar from the second sleeve, leaving the second sleeve in the bone;
    advancing a second bio-absorbable rod into the second sleeve and through the bone block; and
    withdrawing the second sleeve from the bone block and the bone, leaving the second bio-absorbable rod in place;
    wherein the rods retain the bone block, and thereby the piece of tissue, in the bone tunnel; and
    wherein the bio-absorbability of the rods is such as to enable absorption of the rods by a body in which the rods are disposed over time, such that the tissue is initially attached to the bone by the rods and, subsequently, the rods are absorbed into the body.

2. A method according to claim 1 wherein the rods are of a material selected from a group consisting of polylactic acid, polyglycolic acid and polydiaxanone.

3. The method according to claim 1 wherein the rods are formed of a material selected from a group consisting of substantially rigid metals, plastics and ceramics.

4. A method according to claim 1 wherein the trocars each define a tip adapted to drill through the bone by rotation about a longitudinal axis thereof.

5. A method for fixing a piece of tissue in a bone tunnel in a bone, the bone tunnel having a substantially closed distal end and an open proximal end, the method comprising the steps of:
    placing a bone block having the piece of tissue attached thereto in the bone tunnel adjacent the substantially closed distal end of the bone tunnel, with the tissue extending outwardly from the open proximal end of the bone tunnel; and
    advancing a rod through the bone and across the bone tunnel adjacent to a proximal end of the bone block;
    whereby to capture the bone in the bone tunnel between the substantially closed end of the bone tunnel and the rod.

* * * * *